(12) United States Patent
Giraudon et al.

(10) Patent No.: US 7,820,375 B2
(45) Date of Patent: Oct. 26, 2010

(54) USE OF A PROTEIN OF THE CRMP FAMILY FOR TREATING DISEASES RELATED TO THE IMMUNE SYSTEM

(75) Inventors: Pascale Giraudon, Lyons (FR); Marie-Françoise Belin, Lyons (FR); Christophe Malcus, Brignais (FR); Pierre Colas, Saint Didier Au Monte D'or (FR); Jean-Christophe Antoine, Chalain le comtal (FR); Jérôme Honnorat, Bron (FR)

(73) Assignee: Institut National de la Sante Et de la Recherche Medicale (Inserm), Paris (FR)

( * ) Notice: Subject to any disclaimer, the term of this patent is extended or adjusted under 35 U.S.C. 154(b) by 698 days.

(21) Appl. No.: 10/488,554

(22) PCT Filed: Sep. 9, 2002

(86) PCT No.: PCT/FR02/03056

§ 371 (c)(1),
(2), (4) Date: Sep. 13, 2004

(87) PCT Pub. No.: WO03/022298

PCT Pub. Date: Mar. 20, 2003

(65) Prior Publication Data

US 2005/0106143 A1 May 19, 2005

(30) Foreign Application Priority Data

Sep. 7, 2001 (FR) .................................... 01 11627
Oct. 16, 2001 (FR) .................................... 01 13342

(51) Int. Cl.
*C12P 19/34* (2006.01)
*G01N 33/53* (2006.01)

(52) U.S. Cl. .......................................... 435/6; 435/7.1
(58) Field of Classification Search ........................ None
See application file for complete search history.

(56) References Cited

U.S. PATENT DOCUMENTS 7,183,400 B1 * 2/2007 Aguera et al. .............. 536/23.5

2002/0119944 A1 * 8/2002 Aguera et al. .................. 514/44
2003/0077624 A1 * 4/2003 Yang et al. ...................... 435/6

FOREIGN PATENT DOCUMENTS

FR  2805540 A * 8/2001
WO  WO 98/37192 * 8/1998

OTHER PUBLICATIONS

Bolton et al., Mediators of Inflammation, 2006, p. 1-12.*
Furtado et al. Journal of Immunology, 2006, vol. 177, p. 6871-6879.*
Ricard et al., The Journal of Neuroscience, 2001, vol. 21, p. 7203-7214.*
Ladugger 2000 Circulation vol. 102.*
Lowe 2000 Thrombosis and Haemostasis vol. 84.*
Metcalfe 2004 Journal of Clinical Oncology vol. 22.*
Zimmern (2007 Journal of Public Health vol. 1.*
Inatome et al. (Journal of Biological Chemistry, Sep. 1, 2000 vol. 275, p. 27291-27302).*
Ricard et al. (Journal of Neuroscience, Sep. 15, 2001 vol. 21, p. 7214-7213).*
FR2805540 Aguera English translation Translation date Jun. 8, 2010 p. 1-7.*
Quach et al., Collapsin response mediator protein-3/unc-33-like protein-4 gene: organization, chromosomal mapping and expression in the developing mouse brain, (2000), pp. 175-182, vol. 242, Elsevier, Gene.

* cited by examiner

*Primary Examiner*—Zachariah Lucas
*Assistant Examiner*—Agnieszka Boesen
(74) *Attorney, Agent, or Firm*—Stites & Harbison PLLC; Stephen J. Weyer; B. Aaron Schulman

(57) ABSTRACT

The invention concerns the use of at least a protein of the CRMP family, a polypeptide fragment or an active biological derivative thereof, a nucleotide sequence or sequence fragment coding for said protein, an antisense sequence capable of being specifically hybridized with a sequence with nucleotide-type encoding of said protein or an antibody directed against said protein for producing a medicine for treating diseases related to a dysfunction of the immune system. The invention also concerns a method for diagnosing an autoimmune pathology which consists in measuring the expression of a CRMP protein in the lymphocytes.

9 Claims, 10 Drawing Sheets

Figure 1:
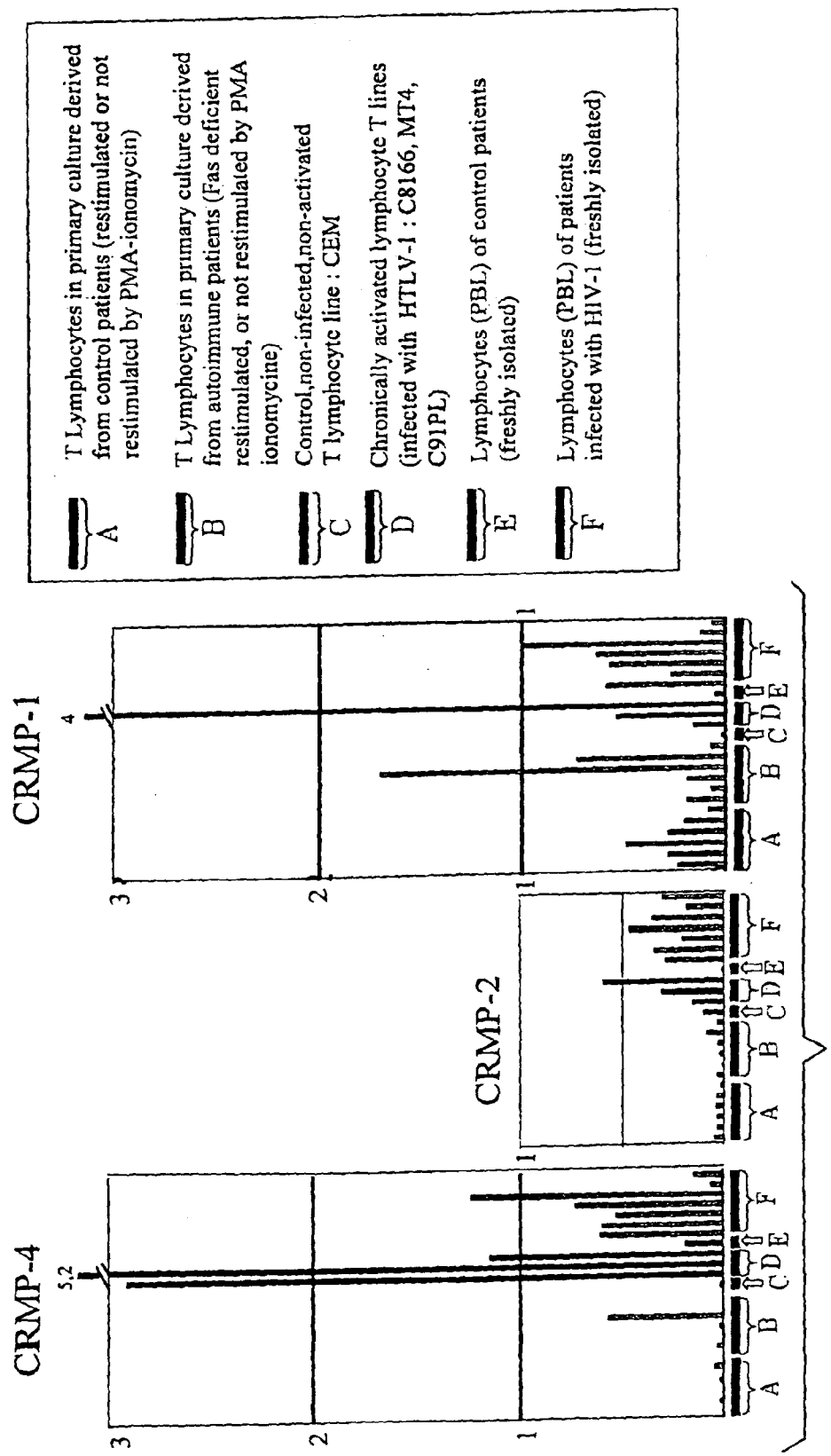

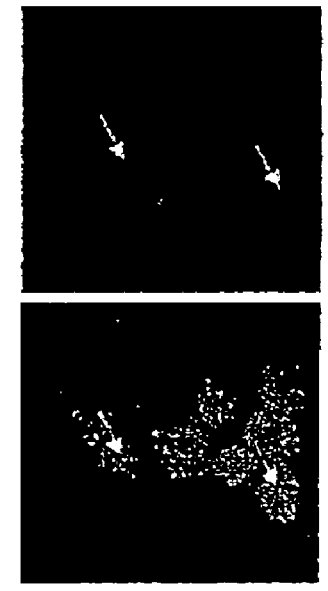
FIG.4a
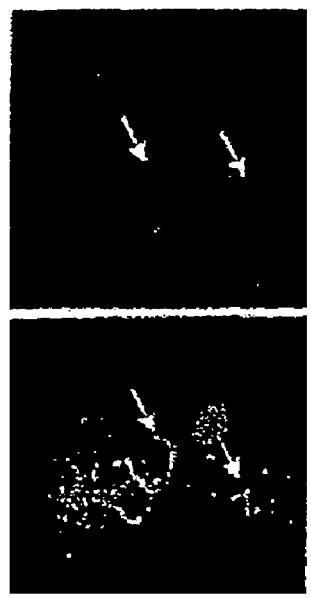
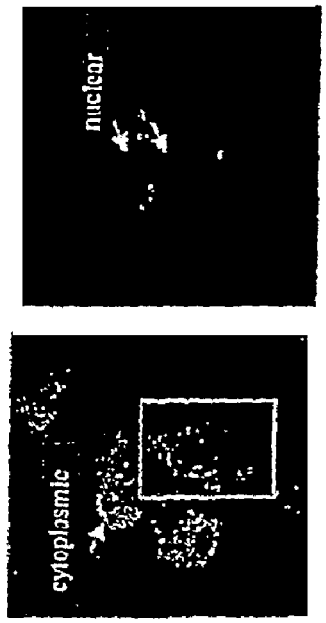
FIG.4b

Peptide sequences for obtaining anti-Ulip antibodies

```
CRMP4    MSYQGKKNIPRITSDRLLIKGGRIVNDDQSFYADIYMEDGLIKQIGDNLI
CRMP2    MSYQGKKNIPRITSDRLLIKGGKIVNDDQSFYADIYMEDGLIKQIGENLI
CRMP1    MSYQGKKSIPHITSDRLLIKGGRIINDDQSLYADVYLEDGLIKQIGENLI
CRMP3    MSFQGKKSIPRITSDRLLIRGGRIVNDDQSFYADVHVEDGLIKQIGENLI
CRMP5    M-------LANSASVRILIKGGKVVNDDCTHEADVYIENGIIQQVGRELM
         *         ..  .* *.**.**...***  .  **. .*.*.*.*.* .*.

CRMP4    VPGGVKTIEANGKMVIPGGIDVHTHFQMPYKGMTTVDDFFQGTKAALAGG
CRMP2    VPGGVKTIEAHSRMVIPGGIDVHTRFQMPDQGMTSADDFFQGTKAALAGG
CRMP1    VPGGVKTIEANGRMVIPGGIDVNTYLQKPSQGMTAADDFFQGTRAALVGG
CRMP3    VPGGIKTIDAHGLMVLPGGVDVHTRLQMPVLGMTPADDFCQGTKAALAGG
CRMP5    IPGGAKVIDATGKLVIPGGIDTSTHFQTFMNATCVDDFYHGTKAALVGG
         .***  * *.*  . .*.***.*   *  ..      *   *** .**.*** **

CRMP4    TTMIIDHVVPEPESSLTEAYEKWREWADGKSCCDYALHVDITHWNDSVKQ
CRMP2    TTMIIDHVVPEPGTSLLAAFDQWREWADSKSCCDYSLHVDISEWHKGIQE
CRMP1    TTMIIDHVVPEPGSSLLTSFEKWHEAADTKSCCDYSLHVDITSWYDGVRE
CRMP3    TTMILDHVFPDTGVSLLAAYERWRERADSAACCDYSLHVDITRWHESIKE
CRMP5    TTMIIGHVLPDKETSLVDAYEKCRGLADPKVCCDYALHVGITWWAPKVKA
         ****..** *.   **  .... .   **   ****.***.*. *     ..

CRMP4    EVQNLIKDKGVNSFMVYMAYKDLYQVSNTELYEIFTCLGELGAIAQVHAE
CRMP2    EMEALVKDHGVNSFLVYMAFKDRFQLTDCQIYEVLSVIRDIGAIAQVHAE
CRMP1    ELEVLVQDKGVNSFQVYMAYKDVYQMSDSQLYEAFTFLKGLGAVILVHAE
CRMP3    ELEALVKEKGVNSFLVFMAYKDRCQCSDSQMYEIFSIIRDLGALAQVHAE
CRMP5    EMETLVREKGVNSFQMFMTYKDLYMLRDSELYQVLHACKDIGAIARVHAE
         *..  *...  ***** ..*..**         . ...*. .      .**.  ****

CRMP4    NGDIIAQEQTRMLEMGITGPEGHVLSRPEELEAEAVFRAITIASQTNCPL
CRMP2    NGDIIAEEQQRILDLGITGPEGHVLSRPEEVEAEAVNRAITIANQTNCPL
CRMP1    NGDLIAQEQKRILEMGITGPEGHALSRPEELEAEAVFRAITIAGRINCPV
CRMP3    NGDIVEEEQKRLLELGITGPEGHVLSHPEEVEAEAVYRAVTIAKQANCPL
CRMP5    NGELVAEGAKEALDLGITGPEGIEISRPEELEAEATHRVITIANRTHCPI
         **...  .    *..******* .*.***.****  * .*** . .**.

CRMP4    YVTKVMSKSAADLISQARKKGNVVFGEPITASLGIDGTHYWSKNWAKAAA
CRMP2    YITKVMSKSSAEVIAQARKKGTVVYGEPITASLGTDGSHYWSKNWAKAAA
CRMP1    YITKVMSKSAADIIALARKKGPLVFGEPIAASLGTDGTHYWSKNWAKAAA
CRMP3    YVTKVMSKGAADAIAQAKRRGVVVFGEPITASLGTDGSHYWSKNWAKAAA
CRMP5    YLVNVSSISAGDVIAAAKMQGKVVLAETTTAHATLTGLHYYHQDWSHAAA
         *. .* *  ....  *. *. .* .*  .*    *  ** ..*. ***

CRMP4    FVTSPPLSPDPTTPDYINSLLASGDLQLSGSAHCTFSTAQKAIGKDNFTA
CRMP2    FVTSPPLSPDPTTPDFLNSLLSCGDLQVTGSAHCTFNTAQKAVGKDNFTL
CRMP1    FVTSPPLSPDPTTPDYLTSLLACGDLQVTGSGHCPYSTAQKAVGKDNFTL
CRMP3    FVTSPPVNPDPTTADHLTCLLSSGDLQVTGSAHCTFTTAQKAVGKDNFAL
CRMP5    YVTVPPLRLDTNTSTYLMSLLANDTLNIVASDHRPFTTKQKAMGKEDFTK
         .** **. *  *.   . **..  *  *..* . * . * ***.**..*.

CRMP4    IPEGTNGVEERMSVIWDKAVATGKMDENQFVAVTSTNAAKIFNLYPRKGR
CRMP2    IPEGTNGTEERMSVIWDKAVVTGKMDENQFVAVTSTNAAKVFNLYPRKGR
CRMP1    IPEGVNGIEERMTVVWDKAVATGKMDENQFVAVTSTNAAKIFNLYPRKGR
CRMP3    IPEGTNGIEERMSMVWEKCVASGKMDENEFVAVTSTNAAKIFNFYPRKGR
CRMP5    IPHGVSGVQDRMSVIWERGVVGGKMDENRFVAVTSSNAAKLLNLYPRKGR
         **.* .* ..**...*.. *  ****** ****** .**** ... ******
```

FIG. 8 (beginning)

```
CRMP4    ISVGSDSDLVIWDPDAVKIVSAKNHQSAAEYNIFEGMELRGAPLVVICQG
CRMP2    IAVGSDADLVIWDPDSVKTISAKTHNSSLEYNIFEGMECRGSPLVVISQG
CRMP1    IAVGSDADVVIWDPDKLKTITAKSHKSAVEYNIFEGMECHGSPLVVISQG
CRMP3    VAVGSDADLVIWNPKATKIISAKTHNLNVEYNIFEGVECRGAPAVVISQG
CRMP5    IIPGADADVVVWDPEATKTISASTQVQGGDFNLYENMRCHGVPLVTISRG
          . *.*.*.*.*   *  ..*    ..*..*  .  .* * * * .*

CRMP4    KIMLEDGNLHVTQGAGRFIPCSPFSDYVYKRIKARRKMADLHAVPRGMYD
CRMP2    KIVLEDGTLHVTEGSGRYIPRKPFPDFVYKRIKARSRLAELRGVPRGLYD
CRMP1    KIVFEDGNINVNKGMGRFIPRKAFPEHLYQRVKIRNKVFGLQGVSRGMYD
CRMP3    RVALEDGKMFVTPGAGRFVPRKTFPDFVIKRIKARNRLAEIHGVPRGLYD
CRMP5    RVVYENGVFMCAEGTGKFCPLRSFPDTVYKKLVQREKTLKVRGVDRTPYL
          .. *.*       * *.. *   *.. .*... *  .   ...* * *

CRMP4    GPVFDLTTTPKG--GTPAGSARGSPTRPN-PPVRNLHQSGFSLSGTQVDE
CRMP2    GPVCEVSVTPKT--VTPASSAKTSPAKQQAPPVRNLHQSGFSLSGAQIDD
CRMP1    GPVYEVPATPKY--ATPAPSAKSSPSKHQPPPIRNLHQSNFSLSGAQIDD
CRMP3    GPVHEVMVPAKP--GSGAPARASCPGKISVPPVRNLHQSGFSLSGSQADD
CRMP5    GDVAVVHPGKKEMGTPLADTPTRPVTRHGG-MRDLHESSFSLSGSQIDD
         * *  .   *   .       *         .*.**.* *****.* *.

CRMP4    GV-RSASKRIVAPPGGRSNITSLS
CRMP2    NIPRRTTQRIVAPPGGRANITSLG
CRMP1    NNPRRTGHRIVAPPGGRSNITSLG
CRMP3    HIARRTAQKIMAPPGGRSNITSLS
CRMP5    HVPKRASARILAPPGGRSS--GIW
          .  .  .*.******..  ..
```

LTSFEKWHEAADTKS : CRMP1 = peptide 6

ITGPEGHVLSRPEEVE : CRMP2 = peptide 3

LEDGTLHVTEGS : CRMP2 = peptide 4

GSARGSPTRPN : CRMP4 =peptide 7

MVPAKPGSGAPARASC : CRMP3 =peptide8

KEMGTPLADTPTRPVTRHGG: CRMP5 =peptide5

IVAPPGGRANITSLG : CRMP2 C-terminal =peptide9

FIG. 8 (end)

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 1
gcaagtgtag gaaggcacgc t                                              21

<210> SEQ ID NO 2
<211> LENGTH: 21
<212> TYPE: DNA
<213> ORGANISM: Artificial sequence
<220> FEATURE:
<223> OTHER INFORMATION: Description of the artificial sequence:
      oligonucleotide

<400> SEQUENCE: 2
ggcagctctg gaacgtgaag a                                              21

<210> SEQ ID NO 3
<211> LENGTH: 20
<212> TYPE: DNA
<213> ORGANISM: Artificial sequence
<220> FEATURE:
<223> OTHER INFORMATION: Description of the artificial sequence:
      oligonucleotide
```

-continued

```
<400> SEQUENCE: 3
cctcagcctt gttcttcacg                                              20

<210> SEQ ID NO 4
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 4
tcacatcaga actcctgtgg                                              20

<210> SEQ ID NO 5
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 5
catgagtgga ggaactttc                                               19

<210> SEQ ID NO 6
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 6
ccatcaccac ccttgtctct                                              20

<210> SEQ ID NO 7
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 7
tcatgctgaa tccacctcgg                                              20

<210> SEQ ID NO 8
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 8
cctctgaggc agttgacgg                                               19

<210> SEQ ID NO 9
<211> LENGTH: 20
<212> TYPE: DNA
<213> ORGANISM: Artificial sequence
<220> FEATURE:
<223> OTHER INFORMATION: Description of the artificial sequence:
      oligonucleotide
```

-continued

```
<400> SEQUENCE: 9
gacatcgcca aggactgact                                              20

<210> SEQ ID NO 10
<211> LENGTH: 19
<212> TYPE: DNA
<213> ORGANISM: Artificial sequence
<220> FEATURE:
<223> OTHER INFORMATION: Description of the artificial sequence:
      oligonucleotide

<400> SEQUENCE: 10 gccgcccta ccagagacc                                                19

<210> SEQ ID NO 11
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 11
gtgcagcgac agccagat                                                18

<210> SEQ ID NO 12
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 12
cggagaaaac ctcatcgt                                                18

<210> SEQ ID NO 13
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 13
ctgggagaga ggagtggttg                                              20

<210> SEQ ID NO 14
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 14
gaagtctcct ccctggacct                                              20

<210> SEQ ID NO 15
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 15
```

```
gttttgtggc cgttaccagt                                              20

<210> SEQ ID NO 16
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 16
ggacttcgag caagagatgg                                              20

<210> SEQ ID NO 17
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 17
acatctgctg gaaggtggac                                              20

<210> SEQ ID NO 18
<211> LENGTH: 22
<212> TYPE: DNA
<213> ORGANISM: Artificial sequence
<220> FEATURE:
<223> OTHER INFORMATION: Description of the artificial sequence:
      oligonucleotide

<400> SEQUENCE: 18
aagtactccg tgtgtggatc gg                                           22

<210> SEQ ID NO 19
<211> LENGTH: 20
<212> TYPE: DNA
<213> ORGANISM: Artificial sequence
<220> FEATURE:
<223> OTHER INFORMATION: Description of the artificial sequence:
      oligonucleotide

<400> SEQUENCE: 19
ggctctccag aacatcatcc                                              20

<210> SEQ ID NO 20
<211> LENGTH: 18
<212> TYPE: DNA
<213> ORGANISM: Artificial sequence
<220> FEATURE:
<223> OTHER INFORMATION: Description of the artificial sequence:
      oligonucleotide

<400> SEQUENCE: 20
ggagattcag tgtggtgg                                                18

<210> SEQ ID NO 21
<211> LENGTH: 24
<212> TYPE: DNA
<213> ORGANISM: Artificial sequence
<220> FEATURE:
<223> OTHER INFORMATION: Description of the artificial sequence:
      oligonucleotide

<400> SEQUENCE: 21
```
gacatcaaga aggtggtgaa gcag        24

<210> SEQ ID NO 22
<211> LENGTH: 15
<212> TYPE: PRT
<213> ORGANISM: Artificial sequence
<220> FEATURE:
<223> OTHER INFORMATION: Synthetic construct

<400> SEQUENCE: 22

Leu Thr Ser Phe Glu Lys Trp His Glu Ala Ala Asp Thr Lys Ser
 1               5                  10                  15

<210> SEQ ID NO 23
<211> LENGTH: 16
<212> TYPE: PRT
<213> ORGANISM: Artificial sequence
<220> FEATURE:
<223> OTHER INFORMATION: Synthetic construct

<400> SEQUENCE: 23

Ile Thr Gly Pro Glu Gly His Val Leu Ser Arg Pro Glu Glu Val Glu
 1               5                  10                  15

<210> SEQ ID NO 24
<211> LENGTH: 12
<212> TYPE: PRT
<213> ORGANISM: Artificial sequence
<220> FEATURE:
<223> OTHER INFORMATION: Synthetic construct

<400> SEQUENCE: 24

Leu Glu Asp Gly Thr Leu His Val Thr Glu Gly Ser
 1               5                  10

<210> SEQ ID NO 25
<211> LENGTH: 11
<212> TYPE: PRT
<213> ORGANISM: Artificial sequence
<220> FEATURE:
<223> OTHER INFORMATION: Synthetic construct

<400> SEQUENCE: 25

Gly Ser Ala Arg Gly Ser Pro Thr Arg Pro Asn
 1               5                  10

<210> SEQ ID NO 26
<211> LENGTH: 16
<212> TYPE: PRT
<213> ORGANISM: Artificial sequence
<220> FEATURE:
<223> OTHER INFORMATION: Synthetic construct

<400> SEQUENCE: 26

Met Val Pro Ala Lys Pro Gly Ser Gly Ala Pro Ala Arg Ala Ser Cys
 1               5                  10                  15

<210> SEQ ID NO 27
<211> LENGTH: 20
<212> TYPE: PRT
<213> ORGANISM: Artificial sequence
<220> FEATURE:
<223> OTHER INFORMATION: Synthetic construct

<400> SEQUENCE: 27

Lys Glu Met Gly Thr Pro Leu Ala Asp Thr Pro Thr Arg Pro Val Thr
 1               5                  10                  15

```
Arg His Gly Gly
            20

<210> SEQ ID NO 28
<211> LENGTH: 15
<212> TYPE: PRT
<213> ORGANISM: Artificial sequence
<220> FEATURE:
<223> OTHER INFORMATION: Synthetic construct

<400> SEQUENCE: 28

Ile Val Ala Pro Pro Gly Gly Arg Ala Asn Ile Thr Ser Leu Gly
  1               5                  10                  15
```

USE OF A PROTEIN OF THE CRMP FAMILY FOR TREATING DISEASES RELATED TO THE IMMUNE SYSTEM

The present invention relates to a novel use of so-called 'CRMPs' (Collapsin Response Mediator Proteins) for the diagnosis and treatment of pathologies related to a dysfunction of the immune system.

CRMPs, also known as TOAD-64 (Minturn et al, 1995, *J Neurosci* 15: 6757-6766), DRP (dihydropyrimidinase related protein, Hamajima et al, 1996, *Gene* 180: 157-163), C-22 (Quach et al, 1997, *Mol Brain Res.* 46: 329-332) or ULIP (Unc-33-Like protein, Byk et al, 1998, *Eur J Biochem* 254: 14-24, and International Application WO 98/37 192), are intracellular signalling molecules that have, until now, been recognised as being specific to the nervous system. These proteins have, in particular, been described as being involved in controlling neuronal development and axonal growth.

Five proteins of this family have been identified to date: CRMP1, CRMP2, CRMP3, CRMP4 and CRMP5.

Certain members of the family have been associated with human neurodegenerative disorders. In Alzheimer's disease, high levels of phosphorylated CRMP2s are thus observed, in conjunction with neurofibril plaques (Yoshida et al, 1998, *J Biol Chem* 273: 9761-9768).

In paraneoplastic neurological syndromes (PNSs), which are neurodegenerative disorders, patients develop auto-antibodies (anti-CV2 antibodies) that recognise CRMPs (Honnorat et al, 1999, *Eur J Neurosci* 11: 4226-4232).

Consequently, it has been proposed to use these proteins in the diagnosis and treatment of cancers and PNSs (FR 2 805 540 and WO 98/37 192).

Yu et al, 2001 (*Annals of Neurology*, 49(2): 146-154), report, furthermore, the presence of anti-CRMP5 neuronal auto-antibodies in cases of lung cancer and thymoma.

Unexpectedly, the inventors have revealed the presence of CRMPs in T lymphocytes. More particularly, they have revealed CRMPs 1, 2 and 4 at high levels in the T lymphocytes in patients affected by dysimmune pathologies. In such cases, it appears that the presence of these proteins is increased when it is associated with a fatal anomaly or an abnormal proliferation of lymphocytes.

Furthermore, the inventors have also observed a markedly increased nuclear translocation of CRMP2 in lymphocytes infected with HTLV-1, probably rendering them hyperproliferative, or T lymphocytes of patients having an immune deficiency related to the Fas/Fas ligand system. This translocation would correspond to a highly phosphorylated form of CRMP2, recognised more particularly by its specific antibody.

Finally, as will emerge from the following examples, the presence of these proteins has also been characterised in thymic epithelial cells, from the embryonic stage. This discovery of CRMPs in immature epithelial cells is one of the rare examples of intracellular signalling protein in the thymus.

Furthermore, the disappearance of CRMPs in the adult thymus and their induction in the T cells after stimulation of the TCR indicates a relationship to the "rearrangement" of the T cell receptor (TCR) and the education of the thymocytes.

Consequently, all of this new data attests to the intervention of CRMPs in a signalling route that leads to the proliferation, death, maturation and education of lymphocytes, and therefore attests to their involvement in regulating the immune response.

These observations are all the more unexpected given that, until now, CRMPs had only been considered, in particular as far as treatment, is concerned, as potential targets for treating pathologies of the central nervous system (CNS).

It is clear that this discovery opens up new perspectives in terms of treatment. It will now be conceivable to act on the proliferation or the death of T cells and/or to act on the cells of the thymus and autoimmunity by intervening at the level of the CRMPs in lymphocytes.

In such cases, the present invention relates specifically to the use of CRMPS as targets for the treatment, prognosis and/or diagnosis of pathologies related to a dysfunction of the immune system and, in particular, the proliferation of T cells.

It relates, in particular, to modulating the expression or the activity of one or more CRMPs in such a way as to modulate the apoptosis, proliferation or migration of the cells.

An alteration of the CRMPs, such as, for example, a modification of the phosphorylation of CRMP2, is thus likely to result in a hyperproliferation or a cell death.

Similarly, stimulation of CRMPs seems to be an effective means for restoring deficient signalling and improving lymphocyte survival, as in the case of HIV infection.

Finally, controlling the hyperexpression of CRMPs seems to be crucial for reducing the proliferation of lymphocytes that have been rendered "hyper"-proliferative, as in the case of an HTLV-1 infection or a Fas mutation. This inhibition might also improve the autoimmune processes that involve T lymphocytes that recognise self determinants (autoreactives), and the attacks on the CNS related to the invasion of the CNS by these T lymphocytes (TSP/HAM related to HTLV-1, encephalitis related to measles, multiple sclerosis).

In certain cases, it is therefore desired to increase or stimulate the expression or the activity of CRMPs (for example, in the case of lymphocytes infected with the AIDS HIV virus). In other cases, on the other hand, it is desired to suppress or inhibit the expression or the activity of CRMPs, in order, for example, to reduce the proliferation or the migration of lymphocytes, for example in the case of a lymphoma.

It may also be advantageous to block CRMP activity, in order to block the effect of the pathological prion protein (PrP).

In a first embodiment, the invention relates to the use of at least one protein of the CRMP family, a polypeptide fragment or biologically active derivative thereof, or of a nucleotide sequence or sequence fragment that encodes said protein, for producing a pharmaceutical composition intended for treating pathologies related to a dysfunction of the immune system.

In another embodiment, the invention relates to the use of an antisense sequence that is capable of hybridising specifically with a sequence that encodes in the manner of a nucleotide manner for said protein or an antibody directed against said protein, for producing a pharmaceutical composition intended to treat pathologies related to a dysfunction of the immune system.

In another embodiment, the invention relates to the use of a peptide sequence that is capable of acting with said protein, or pharmaceutical compounds that are capable of controlling the expression of said protein, and/or their partners and/or their interactions, for producing a pharmaceutical composition intended to treat pathologies related to a dysfunction of the immune system.

The invention also concerns a method for preventing and/or treating a pathology related to a dysfunction of the immune system, this method comprising the administration of a therapeutically effective quantity of an agent that modulates the expression or the activity of a CRMP, in conjunction with a pharmaceutically acceptable vehicle, to a patient requiring a treatment of this type.

Details of these embodiments are given below.

Targeted Pathologies

According to the present invention, the pathologies that are targeted, from the point of view of treatment or diagnosis, are related to a dysfunction of the immune system and, in particular, to a dysfunction of the proliferation of the cells of the immune system, in particular T cells.

More precisely, these pathologies comprise:

T leukaemias (in particular adult T leukaemia) and lymphomas (i.e. the malignant proliferation of T cells);

viral infections, such as an infection with herpes virus, measles virus, Epstein-Barr virus, HTLV-1 (i.e. neuroinflammatory diseases associated with infection with the HTLV1 retrovirus, tropical spastic paraparesis or myelopathy associated with HTLV-1-TSP/HAM), or an infection with the HIV virus (AIDS virus, also called neuro-AIDS). More generally, any viral infection that may result in an invasion of the CNS by T lymphocytes (encephalitis related to measles, etc.) is targeted.

prion diseases.

Dysimmune diseases related to Fas and FasL mutation and neuroinflammatory diseases associated with an activation of lymphocytes are also targeted.

It is also conceivable to treat autoimmune diseases (and, in particular, those related to Fas) by acting, via CRMPs and their various biological partners, on the maturation of the T lymphocytes over the thymus.

Examples of these autoimmune pathologies include, in particular, rheumatoid arthritis, myasthenia gravis, lupus erythematosus, asthma, multiple sclerosis, or any immune disorder involving an immune recognition and the target of cells themselves or of tissues, and resulting in one or more inflammatory responses. Multiple sclerosis is the most common of the autoimmune diseases.

More generally, the invention relates to the treatment or the diagnosis of demyelinating neuroinflammatory diseases.

According to a preferred embodiment of the invention, the patient is a human, preferably an adult, but the treatment method of the invention may also be applied to mammals or other vertebrates.

Modulation of CRMPs

According to the present invention, it is desired to modulate the activity or the expression of CRMPs. This modulation may be direct or indirect.

A direct modulation of the CRMP activity is a modulation that is carried out by direct action on the activity and/or the expression of the protein itself. Agents that are capable of directly modulating CRMP activity are either agonists or antagonists, and may also be referred to as "direct activators" or "direct inhibitors", respectively.

The term "agonist" therefore refers to an agent that increases the activity, while an "antagonist" denotes an agent that inhibits the activity of the protein.

According to a particular embodiment, such agonists or antagonists are capable of modulating the interaction of the CRMP with endogenous molecules, which usually act directly upstream or downstream of the C in a signalling cascade. This may, for example, be a CRMP-semaphorin, CRMP-plexin, CRMP-kinase or alternatively CRMP-(protein of the cytoskeleton) interaction.

Agents of this type are, for example, antibodies directed against the CRMP or aptamers.

An alteration of the interaction between two homologous or heterologous CRMPs is another example of modulation of CRMP activity. An interaction between "homologous" proteins denotes an interaction between at least two identical types of CRMPs, such as, for example, CRMP2-CRMP2 homodimers.

Interaction between "heterologous" CRMPs denotes an interaction between at least two different CRMPS, for example CRMP2-CRMP5 heterodimers.

Agents that are capable of directly modulating the expression of a CRMP include agents that alter (i.e. increase or decrease) the level of production of the CRMP. These agents may, for example, be a CRMP polypeptide or a nucleic acid sequence encoding this protein, or agents capable of modulating the transfection and/or the translation of CRMP genes, such as antisense nucleic acid sequences or inhibiting double-stranded RNA.

An indirect modulation of CRMP activity is a modulation that is carried out by acting on the activity and the expression of extracellular or intracellular endogenous agents, which usually act upstream (inducer) or downstream (effector) of the CRMP, as a signalling cascade. An inducer of a CRMP is, for example, a semaphorin, in particular semaphorin 3A (Sema 3A) or semaphorin 4D (Sema 4D). Examples of effectors include tyrosine kinase, GTPases of the Rho or Rac family, and transferases (transglutaminase).

Other proteins that are capable of interacting with CRMPS, which may be identified in pathological samples, such as cerebrospinal liquid or brain biopsies, in a patient (human or animal) affected by an immunological disorder, also form part of the invention. Agents that allow indirect modulation of the activity or the expression of a CRMP to be obtained may easily be selected by a person skilled in the art, for example in the light of the types of direct modulator described above.

According to the present invention, and unless otherwise stated, the terms "agent" or "test compound" may refer to one or more structurally defined molecules, such as polypeptides, oligonucleotides or an inorganic or organic molecule of an endogenous or exogenous kind. These agents may also be undefined compounds, such as cell or tissue extracts, or biological liquids of animal or vegetable origin.

The use of CRMPs or nucleic acid proteins encoding a CRMP is beneficial when seeking to increase the quantity of at least one of the CRMPs. It is also conceivable to use a compound or a mixture of compounds, of synthetic or natural origin, that activates or inhibits the expression or the action of these CRMPs.

Examples of this type of compound include, in particular, molecules that are capable of acting as a biological partner of CRMPs, using, for example, CRMPs as an intracellular signalling molecule.

CRMPs

The CRMPs considered in particular, according to the invention, are the proteins CRMP1, CRMP2, CRMP3, CRMP4 and CRMP5.

The present invention preferably relates to the use of at least one CRMP selected from the amino acid sequences of the human proteins CRMP1, CRMP2, CRMP3, CRMP4 and CRMP5, which are shown in FIG. 8.

According to the present invention:

the protein CRMP1 refers, in particular, to a protein comprising the amino acid sequence shown in FIG. 8, and also all of the polypeptide fragments or corresponding derivatives.

the protein CRMP2 refers, in particular, to a protein comprising the amino acid sequence shown in FIG. 8, and also all of the polypeptide fragments or corresponding derivatives.

the protein CRMP3 refers, in particular, to a protein comprising the amino acid sequence shown in FIG. 8, and also all of the polypeptide fragments or corresponding derivatives.

the protein CRMP4 refers, in particular, to a protein comprising the amino acid sequence shown in FIG. 8, and also all of the polypeptide fragments or corresponding derivatives.

the protein CRMP5 refers, in particular, to a protein comprising the amino acid sequence shown in FIG. 8, and also all of the polypeptide fragments or corresponding derivatives.

The derived polypeptides refer to any polypeptide variant of the above proteins, or any other molecule resulting from a genetic modification and/or of a chemical nature, of one of the previously specified sequences, i.e. that is obtained by mutation, deletion, addition, substitution and/or any chemical modification of a single amino acid or of a limited number of amino acids, as well any isoform sequence, said derived, modified or isomorphic sequence having retained at least one of the properties rendering it biologically active.

Also included are homologous sequences, defined as:

i) sequences at least 70%, preferably 80%, more preferably 90%, similar to human CRMP sequences (as shown in FIG. 8);

ii) sequences encoded by a homologous nucleic acid sequence, i.e. a nucleic acid sequence hybridising with a sequence encoding human CRMPs or its complementary sequence, under stringent hybridisation conditions.

The term "similar" refers to the perfect likeness or identity between the compared amino acids, but also to the imperfect likeness that is described as similarity. This study of similarities in a polypeptide sequence takes into account conservative substitutions, which are substitutions of amino acids of the same category, such as substitutions of amino acids with non-charged side-chains (such as asparagine, glutamine, serine, threonine and tyrosine), of amino acids with basic side-chains (such as lysine, arginine and histidine), of amino acids with acid side-chains (such as aspartic acid and glutamic acid), and of amino acids with apolar side-chains (such as glycine, alanine, valine, leucine, isoleucine, proline, phenylalanine, methionine, tryptophan and cysteine).

More generally, the term "homologous sequence of amino acids" refers, therefore, to any sequence of amino acids that differs from the human sequence of FIG. 8, by substitution, deletion and/or insertion of an amino acid or a small number of amino acids, in particular by substitution of natural amino acids with unnatural amino acids or pseudo aminoacids, in positions such that these modifications do not significantly impair the biological activity of the CRMP.

Homology is generally determined using a sequence-analysis software package (for example, Sequence Analysis Software Package of the Genetics Computer Group, University of Wisconsin Biotechnology Center, 1710 University Avenue, Madison, Wis. 53705). Similar amino acid sequences are aligned, in order to obtain the maximum degree of homology (i.e. identity or similarity, as defined above). For this purpose, it may be necessary to introduce gaps into the sequence artificially. Once the optimal alignment has been produced, the degree of homology is established by recording all of the positions for which the amino acids of the two compared sequences are identical, in relation to the total number of positions.

The "biological activity" of CRMPs includes any biological property of these proteins. The activity may, for example, be determined by evaluating axonal growth inhibition in response to semaphorins, in particular Sema 3A or Sema 4D, and/or by evaluating inhibition of the growth of oligodendrocytes and/or the migration of cells of the immune system in response to semaphorins. Also included are the immunological properties of CRMPs, in particular the capacity to cause the production of antibodies, of the anti-CV2 type of antibodies, in PNSs. Also included is CRMP enzyme activity, direct or indirect, or as a substrate of another enzyme.

Also concerned are the various forms of proteins that are considered capable of being recognised by their respective antibodies. These may be their dimeric, phosphorylated and/or truncated form.

Figure 5:
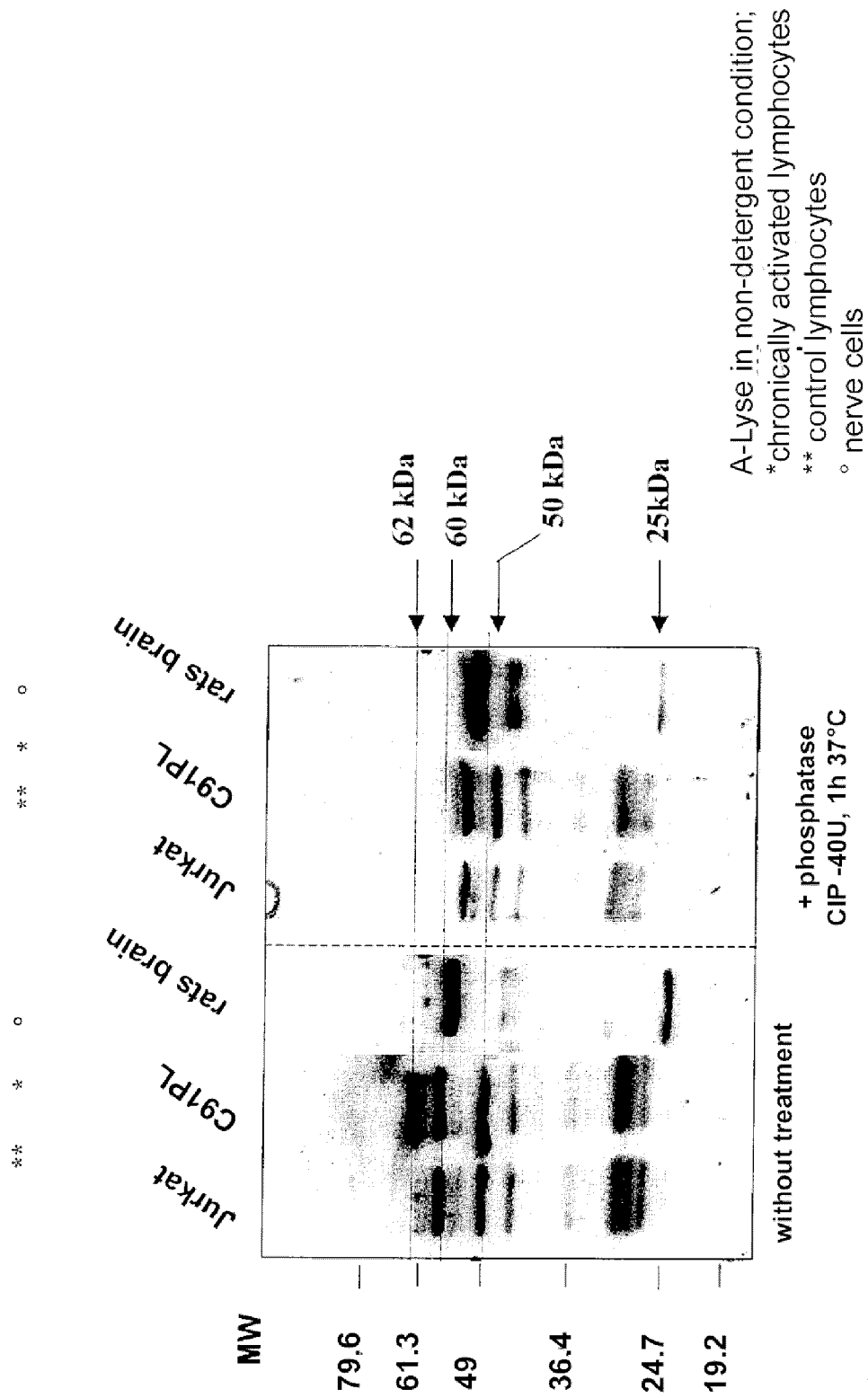

In FIG. 5, the presence of a particular form of phosphorylated CRMP2 is thus demonstrated by a Western blot, using a specific antibody, in the hyperproliferative T lymphocytes infected with the HTLV1 (C91PL) retrovirus, compared to the control lymphocytes (Jurkat).

The proteins CRMP2 and CRMP5 are particularly preferred as therapeutic targets in the present invention. The protein CRMP5, in particular, seems to be an especially beneficial target for the diagnosis and/or treatment of pathologies of the prion disease type.

CRMPs, individually or in a mixture, may be associated with a pharmaceutically acceptable vehicle within a pharmaceutical composition, which may be used for preventing or treating a dysfunction of the immune system.

Nucleic Acids

The invention also covers the use of any sequence of isolated nucleic acids encoding one of the proteins CRMP1, CRMP2, CRMP3, CRMP4 and CRMP5, or nucleotide fragments or sequences deriving from one of the sequences, owing to the degeneration of the genetic code or owing to mutation, deletion or insertion of at least one nucleotide, said derived sequences having a biological activity that is practically identical to that of the protein in question.

The various nucleotide or peptide sequences of the invention may be of artificial or non-artificial origin. They may be DNA or RNA sequences, obtained by screening sequence banks by means of probes developed on the basis of the original sequences. Banks of this type may be prepared by conventional techniques of molecular biology known to a person skilled in the art.

The nucleotide sequences according to the invention may also be prepared by chemical synthesis or alternatively by mixed methods, including the chemical or enzymatic modification of sequences obtained by screening bands. These nucleotide sequences permit the production of nucleotide probes that are capable of hybridising strongly and specifically with a sequence of nucleic acids, of a genomic DNA or a messenger RNA encoding a peptide according to the invention, or a biologically active fragment thereof.

Also included are homologous sequences, defined as:

i) sequences similar to at least 70%, preferably 80%, more preferably 90%, of a sequence encoding a human CRMP (as shown in FIG. 8), or ii) sequences hybridising with a sequence encoding a human CRMP or its complementary sequence, in strict hybridisation conditions.

Preferably, an homologous nucleotide sequence of this type hybridises specifically with complementary sequences of the sequence encoding a CRMP of FIG. 8, under stringent conditions. The parameters defining the stringent conditions depend on the temperature at which 50% of the paired strands separate (Tm).

For sequences comprising more than 30 bases, Tm is defined by the relationship: Tm=81.5+0.41 (% G+C)+16.6 Log (concentration of cations)−0.63 (% formamide)−(600/number of bases) (Sambrook et al, 1989). For sequences less than 30 bases in length, Tm is defined by the relationship: Tm=4 (G+C)+2 (A+T).

Under appropriate conditions of stringency, with which the non-specific sequences do not hybridise, the hybridisation temperature may preferably be from 5 to 10° C. below Tm, and the hybridisation buffers used are preferably solutions with high ionic strength, such as a 6×SSC solution, for example.

The term "similar sequences", used above, refers to the perfect likeness or identity between the compared nucleotides, but also to the imperfect likeness that is described as similarity. This study of similarities in nucleic sequences distinguishes, for example, between purines and pyrimidines.

Homologous sequences of this type include the sequences of genes of mammals other than humans, encoding a CRMP, preferably of a primate, a bovine, ovine or porcine, or alternatively of a rodent, as well as the allelic variants.

A nucleic acid encoding a CRMP may, in particular, be used in gene therapy, in conjunction with a pharmaceutically acceptable vehicle, within a pharmaceutical composition.

Antisenses

The use of anti-CRMP1, CRMP2, CRMP3, CRMP4 and/or CRMP5 antisense sequences is, for its part, favoured when it is desired to block the expression of the CRMP in question.

The nucleotide sequences encoding the proteins CRMP1, CRMP2, CRMP3, CRMP4 or CRMP5 may be used for producing antisense sequences that are capable of hybridising specifically with a sequence of nucleic acids including messenger RNA, which may be used in gene therapy.

The invention therefore also covers the use of antisense sequences that are capable of at least partially inhibiting the production of the CRMPs identified above These sequences may be formulated in pharmaceutical compositions that may be used in gene therapy.

Anti-CRMP Antibodies

The invention also relates to the use of monoclonal or polyclonal antibodies, or fragments thereof, chimeric or immunoconjugated antibodies obtained from a CRMP selected from the proteins CRMP1, CRMP2, CRMP3, CRMP4 and CRMP5, and biologically active polypeptide derivatives or fragments of CRMPs.

The antibodies may be used for blocking the expression of the CRMP in question.

The polycolonal antibodies may be obtained according to the protocol described in the examples. These antibodies may, however, also be obtained using conventional methods.

The polycolonal antibodies may be obtained from the serum of an animal immunised against a polypeptide according to the common operating procedures.

According to one embodiment of the invention, an appropriate peptide fragment, as defined above, which is capable of being coupled via a reactive residue to a protein or another peptide, may be used as an antigen. Rabbits were immunised with the equivalent of 1 mg of peptide antigen, according to the procedure described by Benoit et al., PNAS USA, 79, 917-921 (1982). The animals were treated with injections of 200 μg of antigen at four week intervals and bled 10 to 14 days later. After the third injection, the antiserum was examined, in order to determine its capacity to bind to the antigen peptide radioactively-labelled with iodine, prepared according to the chloramine-T method, and then purified by chromatography over a carboxymethyl cellulose (CMC) ion exchange column.

The antibody molecules were then collected from the mammals and isolated to the desired concentration by methods that are well-known to a person skilled in the art, for example using DEAE Sephadex in order to obtain the IgG fraction.

In order to increase the specificity of the polyclonal serum, the antibodies may be purified by immuno-affinity chromatography, using polypeptides that immunise in the solid phase. The antibody is placed in contact with the polypeptide that immunises in the solid phase for a sufficient period of time to make the polypeptide immuno-react with the antibody molecule, in order to form an immunological complex in the solid phase.

Examples of the sequences used to produce these antibodies include, in particular, those shown in FIG. 8.

These are:
peptide 6 (CMRP1): SEQ ID no 22;
peptide 3 (CMRP2): SEQ ID no 23;
peptide 4 (CMRP2): SEQ ID no 24;
peptide 7 (CRMP4): SEQ ID no 25;
peptide 8 (CRMP3): SEQ ID no 26;
peptide 5 (CRMP5): SEQ ID no 27;
peptide 9 (CRMP2 C-terminal): SEQ ID no 28.

Anti-peptide 4 is more specific to CRMP2, which is particularly advantageous given the strong homology between CRMPs, which makes specific antibodies difficult to produce. The peptide comprises a serine that is a potential phosphorylation site and that is likely to facilitate detection of the phosphorylated form.

Anti-peptide 9 (CRMP2 C-terminal) is also specific to one part of the protein CRMP2, which is truncated in certain pathological circumstances.

Anti-peptide 5 is specific to CRMP5 and therefore advantageously allows CRMP5 to be distinguished from other CRMPs.

Monoclonal antibodies, which may, for example, be obtained by the conventional hybridoma culture method of Köhler and Milstein, *Nature,* 256, 495-497, (1975), may also be used.

The antibodies may be chimeric antibodies, humanised antibodies, or Fab and F(ab')2 fragments. They may also be in the form of immunoconjugates or labelled antibodies.

Anti-CRMP antibodies may be used in conjunction with a pharmaceutically acceptable vehicle, in pharmaceutical compositions that may be used for the prevention or treatment of a dysfunction of the immune system. They may also be used as a diagnostic tool.

Interaction with Other Partners

It is also conceivable to intervene in the signalling cascade by using a compound or mixture of compounds, of synthetic or natural origin, that is capable of inhibiting the action of said CRMPs and, more particularly, of blocking interaction, either between two of said proteins, or between one of said proteins and its natural biological partners.

More generally, it is conceivable to use CRMPs as baits for identifying new therapeutic targets in biological extracts, of the lipid or biopsy type, from patients affected by autoimmune or neuroinflammatory diseases, lymphomas or T leukaemias.

The invention also relates to the use of at least one CRMP as a diagnostic tool for detecting, identifying and/or analysing at least one biological partner of a CRMP in biological extracts from patients affected by autoimmune or neuroinflammatory diseases, lymphomas or T leukaemias.

The inventors have thus demonstrated that CRMPs, which are intracellular signalling molecules, react with the PrP prion protein, which is involved in membrane signalling.

It is likely that the modulation of the expression of CRMPs in the lymphocytes via the PrP protein would occur, in the degeneration process, at the level of the transfer of pathogenic information from the immune system toward the central nervous system. This aspect of the invention is illustrated by example 4 (below).

As a biological partner of CRNPs, the PrP protein may also be a beneficial target for modulating the activity of CRMPs. The therapeutic approach in question would therefore consist in blocking interaction between the PrP and the CRMP, in particular CRMP5.

In such cases, another aspect of the invention relates to a pharmaceutical composition comprising, specifically by way of an active ingredient, a compound or mixture of compounds, of synthetic or natural origin, that is capable of targeting at least one CRMP and/or of inhibiting the natural interaction of at least one CRMP and/or a CRMP dimer with the PrP prion protein.

According to one particular embodiment of the invention, the CRMP in question is CRMP5.

In the sense of the invention, the compound or mixture of compounds acts, more particularly, by blocking interaction between the two proteins in question. The so-called aptamer compounds are particularly suitable for this purpose. These are molecules that have the ability to bind to other molecules with great affinity and specificity. Examples of this type of compound include, in particular, peptide aptamers.

Pathologies that are capable of being treated according to this variant are sporadic, acquired or genetic prion diseases or, more generally, any disease involving PrP in cellular signalling.

Compounds possessing a stimulating or inhibiting activity with regard to CRMPs may be selected using a screening method, in which the compound to be tested is placed in contact with a CRMP, and the interaction between the two proteins determined.

The invention also relates to a method for the in vitro screening of molecules that may be used for the treatment of prion diseases, wherein a molecule to be tested is placed in contact with a PrP prion protein and a CRMP, and the capacity of the molecule to inhibit the interaction of the CRMP, or of a CRMP dimmer, with the PrP protein is evaluated, an inhibiting action on this interaction being indicative of a molecule that may be used for the treatment of prion diseases.

Administration

The optimal modes of administration, dosages and galenical forms of the pharmaceutical compositions according to the invention may be determined according to the criteria that are generally taken into account when establishing a suitable therapeutic treatment for a patient, such as, for example, the age and body weight of the patient, his general state of health, treatment tolerance, recorded side effects, etc.

Preferably, the pharmaceutical compositions according to the invention may be administered systemically, preferably intravenously, intramuscularly, intradermally or orally.

Generally, a therapeutically or prophylactically effective quantity varying from around 0.1 µg to around 1 mg of CRMP may be administered to human adults.

The invention also relates to a pharmaceutical composition comprising a nucleic acid, as defined above, encoding a CRMP or an antisense nucleic acid and a pharmaceutically acceptable vehicle, said composition being intended to be used in gene therapy. The nucleic acid, which is preferably inserted into a, generally viral, vector (such as adenoviruses and retroviruses), may be administered in naked form, without any vehicle promoting the transfer to the target cell, such as anionic liposomes, cationic lipids, microparticles, for example gold microparticles, precipitating agents, for example calcium phosphate, or any other agent facilitating transfection. In this case, the polynucleotide may simply be diluted in a physiologically acceptable solution, such as a sterile solution or a sterile buffer solution, in the presence or in the absence of a vehicle.

Alternatively, a nucleic acid of the invention may be associated with agents that facilitate transfection. It may, inter alia, be (i) associated with a chemical agent that modifies cellular permeability, such as bupivacaine; (ii) encapsulated in liposomes, possibly in the presence of additional substances facilitating transfection; or (iii) associated with cationic lipids or silica, gold or tungsten microparticles.

If the nucleic acid constructions of the invention cover microparticles, said microparticles may be injected intradermally or intraepidermally, by the "gene gun" technique (WO 94/24263).

The quantity to be used as medicine depends, in particular, on the nucleic acid construction itself, on the individual to whom this nucleic acid is administered, on the mode of administration and type of formulation, and on the pathology. Generally, a therapeutically or prophylactically effective quantity varying from around 0.1 µg to around 1 mg, preferably from around 1 µg to around 800 µg, preferentially from around 25 µg to around 250 µg, may be administered to human adults.

The nucleic acid constructions of the invention may be administered by any conventional administration route, such as, in particular, parenterally. The choice of the route of administration depends, in particular, on the selected formulation.

Diagnostic Methods

The invention also relates to an in vitro method for the prognosis and/or diagnosis of a pathology related to a dysfunction of the immune system, the method comprising the revelation, in cells of the immune system, i.e., in particular, lymphocytes, dendritic cells and monocytes taken from a patient (for example, from the blood or the brain), of an abnormal expression or location of the CRMP relative to the control lymphocytes.

The invention relates, more precisely, to a method for the prognosis and/or diagnosis of autoimmune diseases, lymphomas, adult leukaemia, neuroinflammatory diseases, which may or may not be related to a viral infection, and/or prion diseases, characterised in that the presence of at least one CRMP, the expression, sequence or location of which is modified relative to the control lymphocytes obtained from healthy subjects, is revealed in lymphocytes taken from an individual.

Any pathology related to a dysfunction of T lymphocytes, as described above, may thus be diagnosed.

In particular, it may be determined whether an individual is a carrier of, or is likely to develop, a pathology selected from:
  T leukaemias and (T) lymphomas;
  viral infections, such as herpes virus, measles virus, Epstein-Barr virus, HTLV-1 or HIV;
  prion diseases;
  and demyelinating neuroinflammatory diseases.

The expression of CRMPs may be evaluated by various techniques that are well-known to a person skilled in the art. The RNA encoding the proteins may be detected and quantified using specific nucleotide probes.

According to the first embodiment, the invention relates to a method for the in vitro diagnosis of a pathology related to a dysfunction of the immune system, or of a predisposition to develop a pathology related to a dysfunction of the immune system, comprising the stages consisting in:
bringing together a biological sample containing mRNA, obtained from lymphocytes in a patient, with specific oligonucleotides allowing the amplification of all or part of the transcript of the encoding gene for a CRMP;
amplifying said transcript,
detecting and quantifying the amplification products;

a modification of the transcript rate of the CRMP relative to a normal control being indicative of a pathology related to a dysfunction of the immune system, or of a predisposition to develop such a pathology.

The products of the encoding genes for the CRMPs may also be analysed using corresponding antibodies, as described above, and located in the cell.

According to this second embodiment, the invention relates to a method for the in vitro diagnosis of a pathology related to a dysfunction of the immune system, or of a predisposition to develop a pathology related to a dysfunction of the immune system, for detecting or measuring the rate of CRMP expression and/or activity in a sample of lymphocytes of a patient, using anti-CRMP antibodies. This method comprises the placing in contact of at least one antibody directed against CRMP with said sample under conditions which allow the possible formation of specific immunological complexes between the CRMP and said antibody or antibodies and the detection of the specific immunological complexes possibly formed and/or the inhibition of CRMP activity by the antibody.

Alternatively, the presence of the anti-CRMP antibodies may be determined by means of the CRMPs or their epitopic fragments which may be labelled in such a way that the complexes formed between the proteins and said antibodies may then be detected easily in biological samples.

The following examples and figures are presented to illustrate but not limit the present invention.

FIGURES

FIG. 1: comparison by RT-PCR analysis of the level of expression of the mRNA encoding CRMP-4, -2 and -1 in mononucleated or control lymphocytes and cells or in those derived from patients affected by dysimmune pathologies. The level of expression of the CRMP mRNA is standardised relative to the level of expression of the GAPDH ubiquitary gene. The results are expressed as a relative value as a ratio of pixels between the amplicon of each CRMP and the amplicon of G3PDH.

Figure 2:
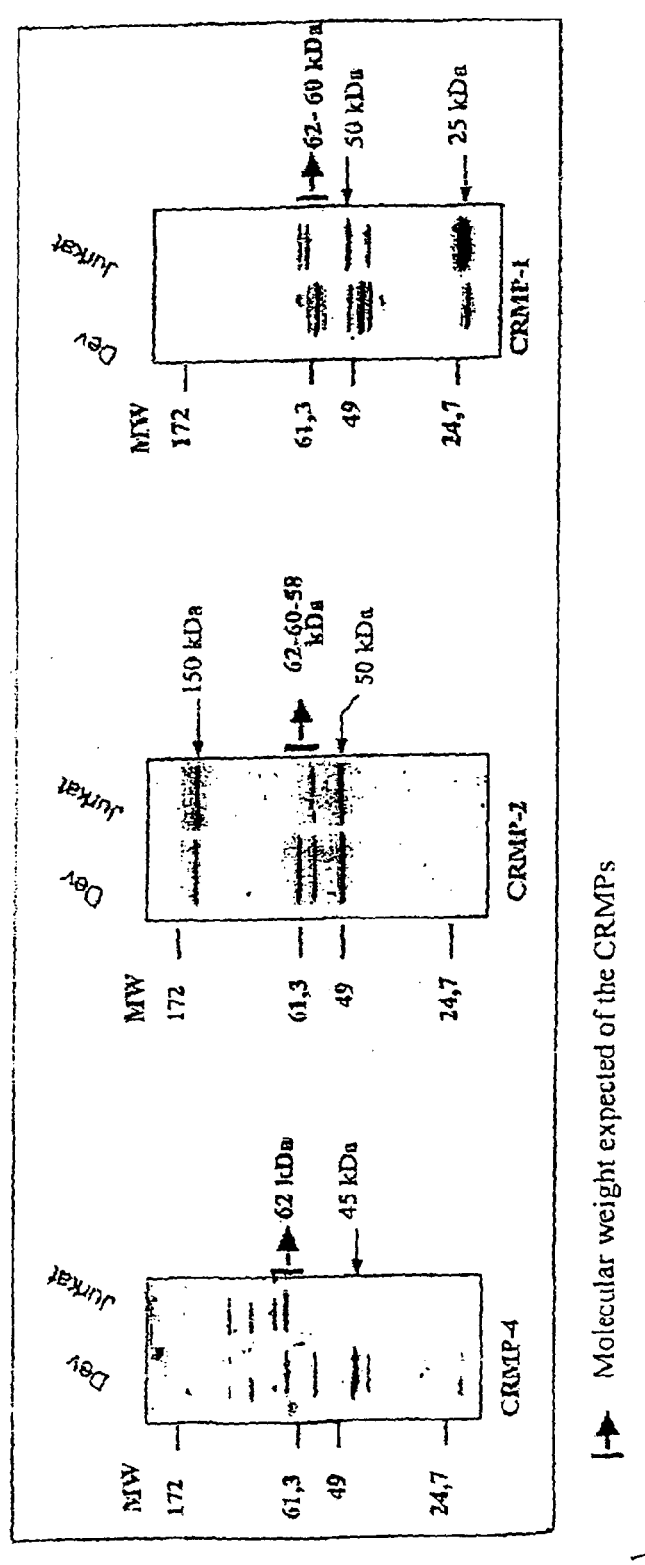

FIG. 2: electrophoretic profile of the CRMP 1, 2 and 4 proteins in a Jurkat lymphocyte line compared with a Dev nerve cell line.

Figure 3:
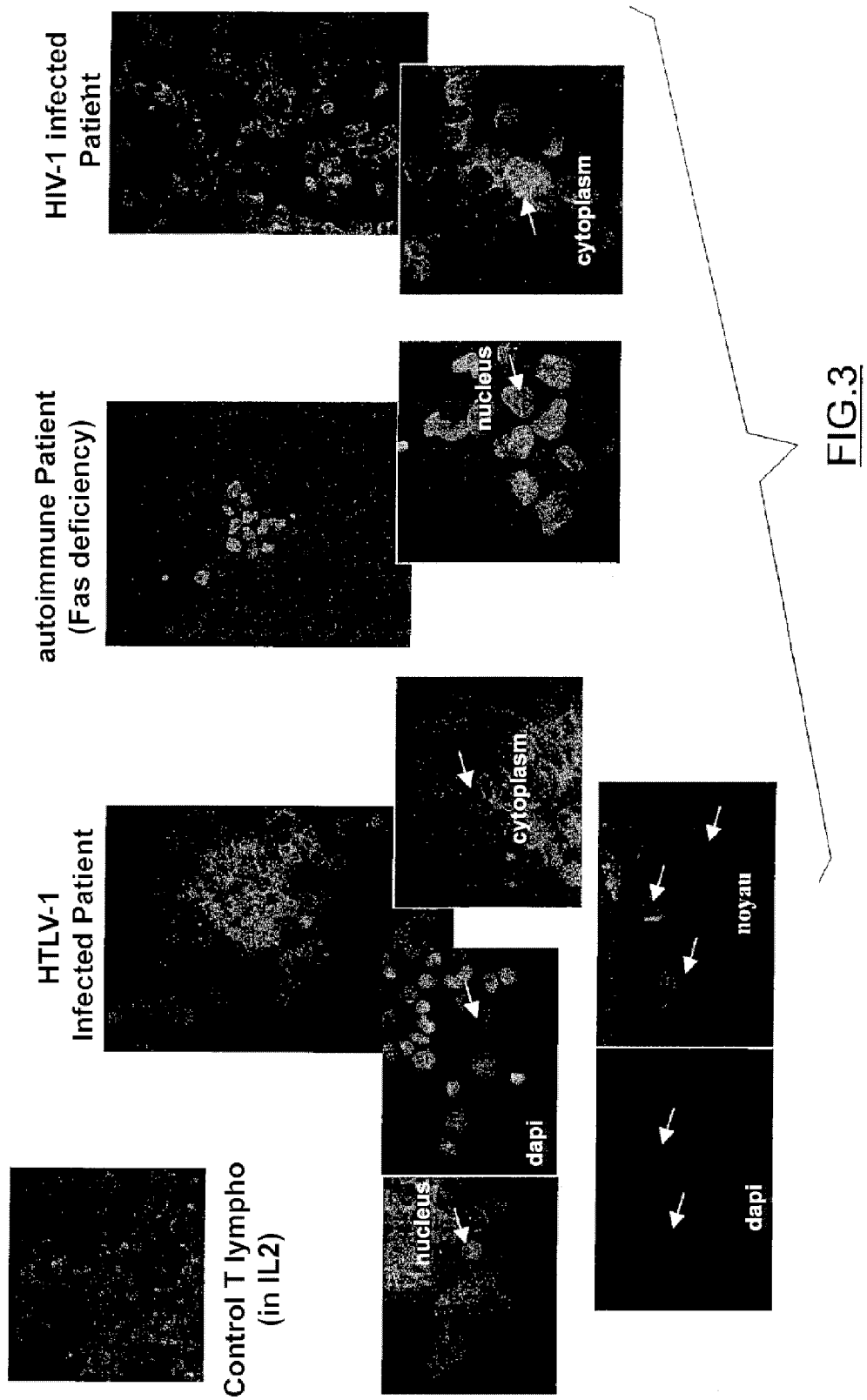

FIG. 3: immunocytochemical detection of the subcellular location of the CRMP2 protein in mononucleated blood cells (PBL) of control patients or patients infected with HTLV-1 or having an immune deficiency associated with the Fas/Fas ligand system, or infected with HIV.

FIG. 4: characterisation of the nuclear presence recognised by the anti CRMP-2 (peptide 4) in the hyperproliferative T lymphocytes.

FIG. 4a: examination after immunodetection of CRMP-2 and counter-staining by the intercalator of the Dapi DNA in the Jurkat T cells (controls) and the C 8166 cells (T infected by HTLV-1 which do not produce viruses).

FIG. 4b: examination of the immunodetection of CRMP-2 by confocal microscopy in the CEM cells (control line T) and the C91PL cells (line infected with HTLV-1).

FIG. 5: demonstration by a Western blot using specific anti-CRMP2 antibodies (peptide 4) of the presence of a particular form of phosphorylated CRMP2 in the hyperproliferative T lymphocytes (C91PL) compared with the control lymphocytes (Jurkat).

Figure 6:
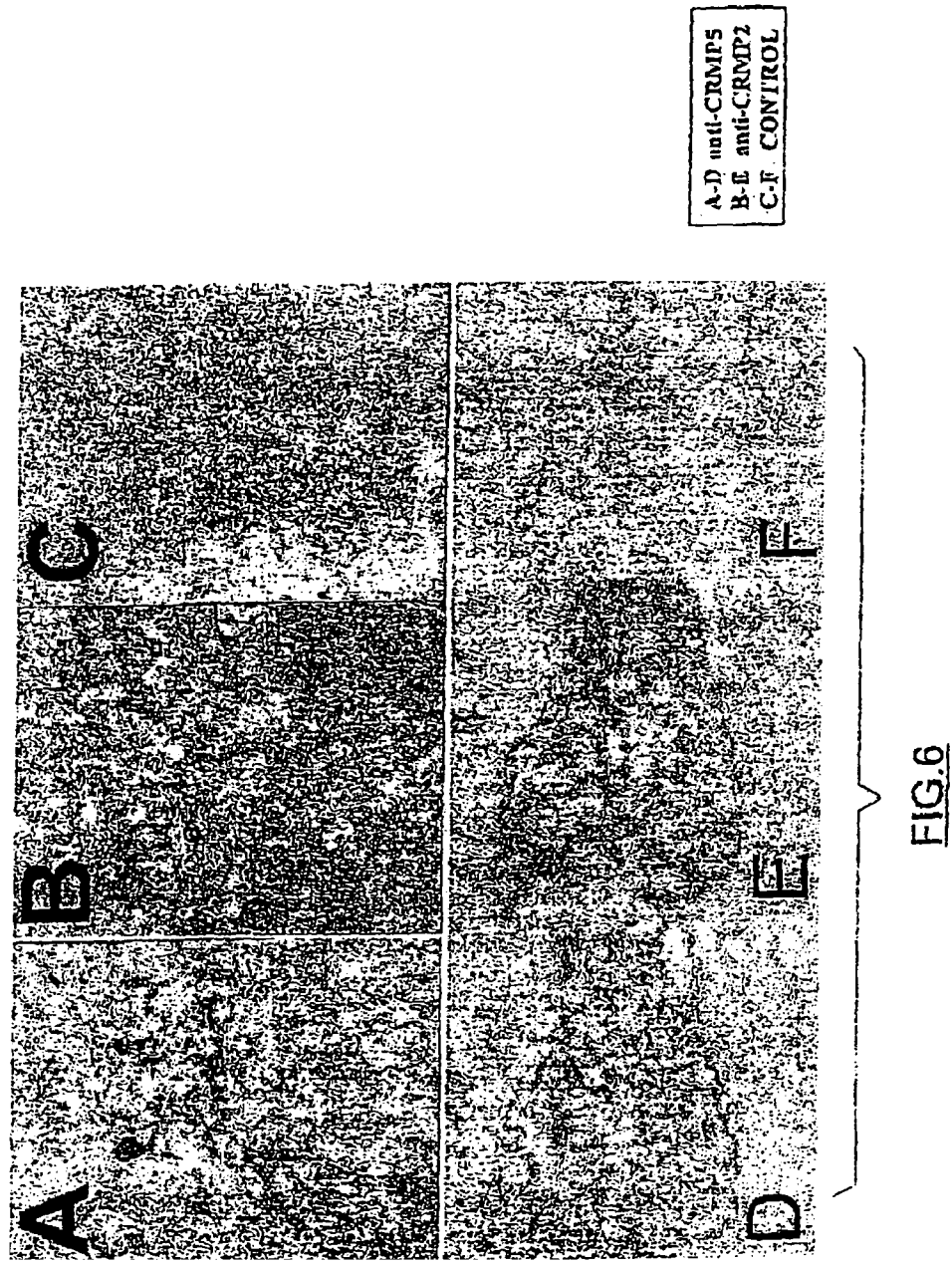

FIG. 6: immunohystochemical analysis of the expression of the CRMP5 and CRMP2 proteins over the human foetal thymus (A, B, C) and in a thymoma (D, E, F).

Figure 7:
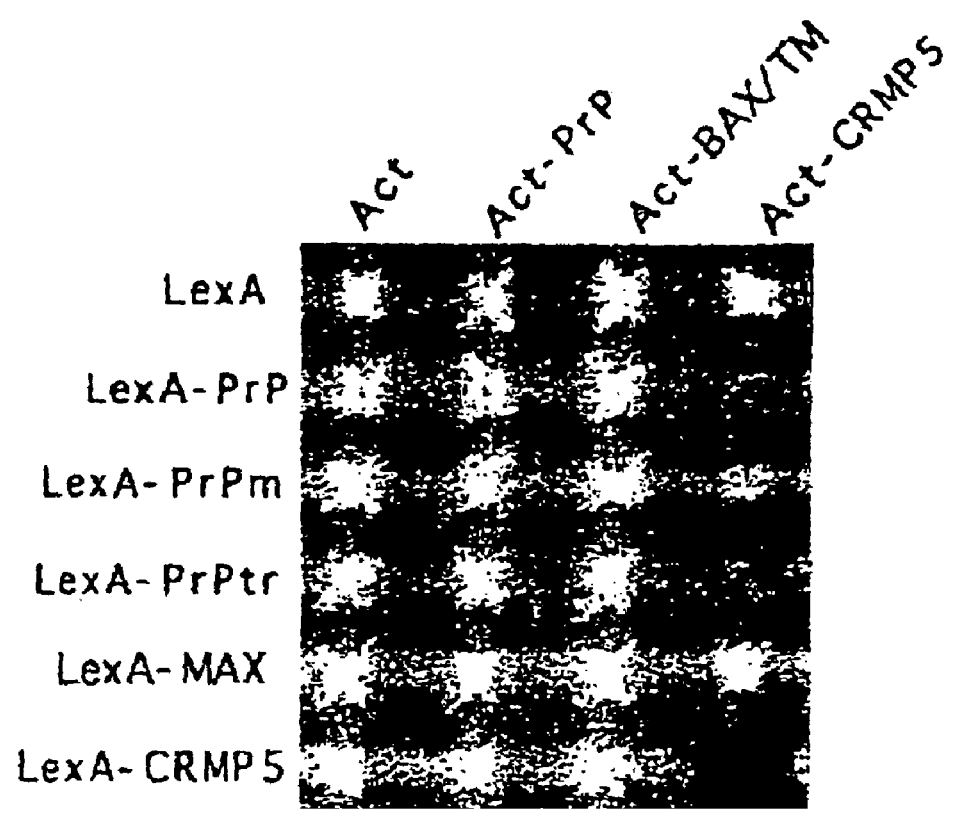

FIG. 7: characterisation by two-hybrid tests by conjugation of the interaction between the bovine PrP protein and the human CRMP5 protein.

FIG. 8: amino acid sequences of the human proteins CRMP1, CRMP2, CRMP3, CRMP4 and CRMP5. This figure also shows the sequences of the peptides selected to produce the antibodies specifically directed against the CRMPs.

Figure 9:
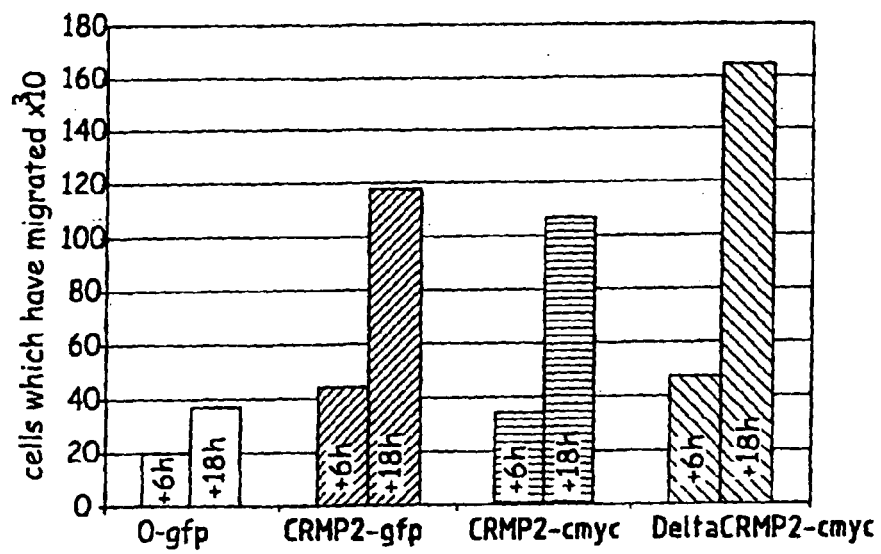

FIG. 9 shows the migration kinetics of T lymphocytes transfected or not transfected with a vector encoding CRMP-2.

Figure 10:
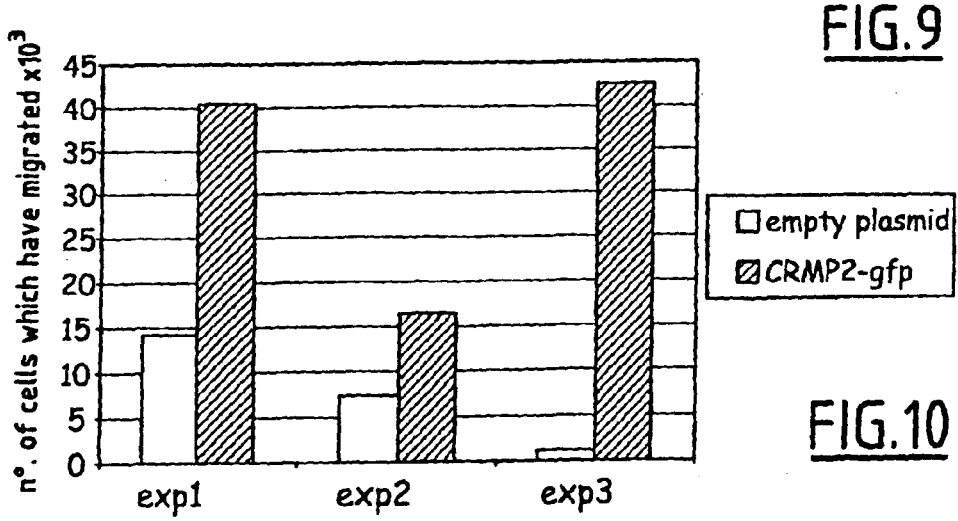

FIG. 10 reports the number of T cells which have migrated in three experiments, after over-expression of CRMP-2 gfp.

Figure 11:
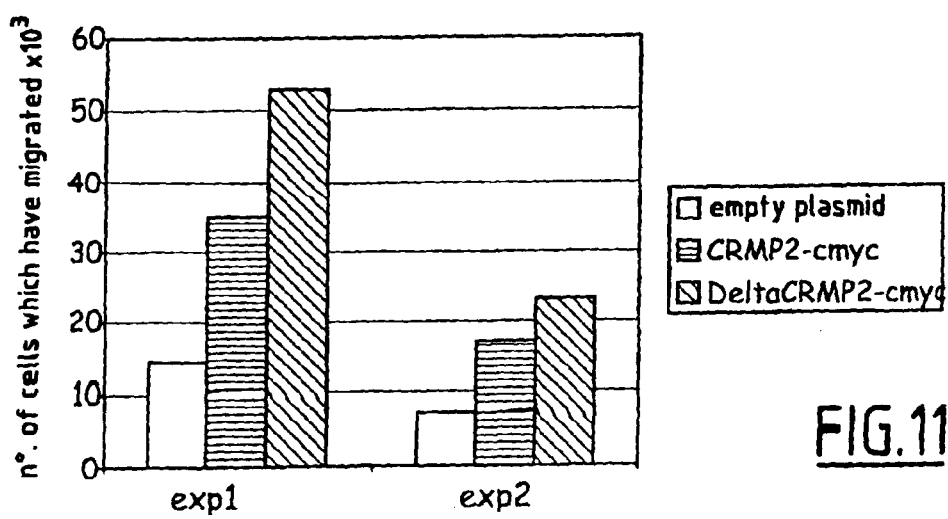

FIG. 11 reports the number of T cells which have migrated in two experiments, after transfection of CRMP-2 plasmids associated with cmyc and mutated CRMP-2 (Delta 381CRMP2-cmyc).

EQUIPMENT AND METHODS

1. Cells and Cell Culture

SI cells: the T lymphocytes are either lymphocytes established in lines. (IL-2 independent) or lymphocytes in primary culture, the growth of which necessitates the presence of IL-2. These lymphocytes are cultivated (37° C., 5% $CO_2$) in suspension in a supplemented saline medium, namely in SVF (10%) in the case of lymphocyte lines, in AB type human serum (SAB 10%) and in IL-2 in the case of primary cultures of T lymphocytes. Peripheral blood lymphocytes (PBL) have also been freshly isolated from the blood of control patients or subjects, separated over a Ficoll gradient and recovered after a phase of adhesion of the monocytes/macrophages.

Treatments of the T lymphocytes: for certain experiments, the freshly isolated PBLs were treated with agonistic CD3 antibodies (10 µg/ml) which mimic the activation of the lymphocytes by an antigen via the T receptor (TCR) or by the phytohemagglutinin (PHA-10 µg/ml) (C. Malcus).

2. Examination of Transcripts (mRNA) by the RT-PCR (Reverse Transcription and Polymerase Chain Reaction) Method Isolation of the total RNA: this experiment is carried out systematically at 4° C. to avoid degradation of the RNAs by the Rnases. RNA was extracted from cell cultures or from freshly isolated lymphocytes to which a solution of RNAzol is added (2 ml per $10^6$ cells). The RNAzol contains the phenol and the guanidium isothiocyanate and lyses the cells. The phase is separated using chloroform (400 µl per 2 ml of RNAzol). After homogenisation (vortex) then 5 minutes of rest, the sample is centrifuged at rest (5 minutes), then centrifuged at 12,000 rpm, for 30 minutes at 4° C. The RNAs present in the aqueous phase (measured volume) are precipitated first by addition of an identical volume of isopropanol (15 min at 4° C.) then centrifugation (12,000 rpm for 15 minutes at 4°

C.). A second precipitation is carried out by adding a volume of 0.3 M sodium acetate pH 5.2 and three volumes of absolute ethanol at −20° C., to the pellet. The precipitate is collected by centrifugation (12,000 rpm, 15 minutes, 4° C.). the salts are removed by adding 800 µl of 80% ethanol at −20° C., to the pellet followed by centrifugation. After removing all traces of ethanol, the pellet is dissolved in 100 µl of distilled water and stored at −80° C. The RNAs are analysed by measuring the optical density using a spectrophotometer at 260 and 280 nm (1 unit of OD at 260 nm=40 µg of RNA). The ratio of the ODs obtained at 260 nm and at 280 nm should be close to 2, which is an indication of good RNA extraction without a trace of proteins.

Reverse transcription: reverse transcription (RT) is the stage preliminary to iterative polymerisation which uses a polymerase DNA that is incapable of polymerising DNA from RNA. RT is carried out using a reverse transcriptase, the Rtase of the MuLV virus, and is initiated by a primer which allows the elongation and synthesis of one complementary strand of DNA of the RNA by the The products of RT are then diluted to $^{10}/_{10}{}^{th}$ in distilled water and stored at −20° C.

The polymerisation chain reaction (PCR): iterative polymerisation is a technique which involves repeating the polymerisation cycles of a segment of a DNA which is of interest. The first stage of each cycle is a denaturation stage carried out at 95° C. The second stage is a hybridisation or attachment stage with specific primers of the segment which enclose the region to be amplified at a temperature at which 50% of the DNA are in double-stranded form and the remaining 50% in single-stranded form (Tm). The third stage is the stage of elongation at 72° C. which is the optimum temperature for the activity of thermostable DNA dependent DNA polymerase, Taq polymerase. The parameters which have to be taken into consideration as a priority to optimise the PCR are the choice of the primers (performed by the Primer 3 software and validated by comparison with indexed human sequences, Blast), the hybridisation temperature or Tm, the concentration of $MgCl_2$ and the number of cycles. All these conditions were perfected before carrying out the PCRs and are summarised in the following Table:

| | Primers for RT-PCR Probe for the Southern blot | | | Tm | [MgCl$_2$] | Number of cycles |
|---|---|---|---|---|---|---|
| CRMP-4 | Sense: gcaagtgtaggaaggcacgct SEQ ID NO 1 | Antisense: ggcagctctggaacgtgaaga SEQ ID NO 2 | Probe: cctcagccttgttcttcacg SEQ ID NO 3 | 62° C. | 2 mM | 28 |
| CRMP-2 | Sense: tcacatcagaactcctgtgg SEQ ID NO 4 | Antisense: catgagtggaggaactttc SEQ ID NO 5 | Probe: ccatcaccaccttgtctct SEQ ID NO 6 | 62° C. | 3 mM | 22 |
| CRMP-1 | Sense: tcatgctgaatccacctcgg SEQ ID NO 7 | Antisense: cctctgaggcagttgacgg SEQ ID NO 8 | Probe: gacatcgccaaggactgact SEQ ID NO 9 | 62° C. | 3 mM | 26 |
| CRMP-3 | Sense: gccgccctaccagagacc SEQ ID NO 10 | Antisense: gtgcagcgacagccagat SEQ ID NO 11 | Probe: cggagaaaacctcatcgt SEQ ID NO 12 | 62° C. | 3 mM | 30 |
| CRMP-5 | Sense: ctgggagagaggagtggttg SEQ ID NO 13 | Antisense: gaagtctccLccctggacct SEQ ID NO 14 | Probe: gttttgtggccgttaccagt SEQ ID NO 15 | 62° C. | 3 mM | 28 |
| Actine | Sense: ggactlcgagcaagagatgg SEQ ID NO 16 | Antisense: acatctgctggaaggtggac SEQ ID NO 17 | Probe: aagtactccgtgtgtggatcgg SEQ ID NO 18 | 62° C. | 3 mM | 25 |
| G3PDH | Sense: ggctctccngmacatcatcc SEQ ID NO 17 | Antisense: ggagattcaglgtggtgg SEQ ID NO 18 | Probe: gacatcnngaaggtggtgaagcag SEQ ID NO 19 | 62° C. | 3 mM | 23 | enzyme. In a comparison study of the products of amplification of various mRNAs, the use of the non-specific primers (oligodT) was found to be more suitable, affording the possibility of leading the various specific PCRs from a same sample of RT.

500 ng of total RNA diluted in 7 µl of water (QS) are incubated for 10 minutes at 70° C. to allow the denaturation of the secondary structures, then the tubes are immediately plunged into ice to prevent renaturation. To these 70 µl of total RNA there are then added 1 µl of oligodT (100 mg/µl) and 12 µl of "incubation" medium containing 0.5 mM of dNTP, 4 µl of RT buffer, 40 U of RNAsine (Rnase inhibitor), 10 mM of dithiothreitol or DTT (denaturant), 1 µl of MuLV-Rtase (200 U/µl). The reaction mixture is incubated for 90 minutes at 42° C.

Each sample of PCR contains 10 µl of RT diluted to $1/10^{th}$ and 40 µl of Mix, 5 µl of PCR 1× buffer, 2 or 3 µl of $MgCl_2$, 4×1 µl of dNTP, 1 µl of each primer (sense and antisense), 0.4 µl of Taq polymerase, QS 50 µl of distilled water. The PCR comprises a first stage of denaturation for: 5 min at 95° C. then a predetermined number of cycles for each pair of primers (cf. Table) (1 min at 95° C., 1 min 15 at 62° C., 1 min 30 at 72° C.). The PCR ends with an elongation stage of 15 min at 72° C. and the PCR products are stored at −20° C.

Visualisation of the RT-PCRs: Southern blot: it is carried after separation of the amplification products by electrophoresis and then transfer to a membrane and hybridisation with an internal radioactively labelled probe. The migration of the various PCR products is effected by depositing 10 μl of each sample on a 1.5% agarose gel in a TBE (Tris-Borate-EDTA) buffer 0.5× containing ethidium bromide (0.5 μg/ml at the end) and application of 100 V. Once migration has occurred, the cDNA are transferred onto a nylon membrane in TBE 0.5× buffer by a semi-dry electrotransfer method. After transfer (15V—45 min), the DNA is fixed to the membrane by a solution of NaOH (0.4N—2 min) then neutralised (SSC 6×—10 min). The internal probe, which is specific for the DNA fragment amplified by PCR (cf. Table) is radioactively labelled at 5' by a terminal kinase (T4 kinase) with γ32P-ATP. 2 μl are incubated for 10 min at 37° C. with 5 μl of forward buffer, 1 μl of T4 kinase, 2 μl of γ32P-ATP and 15 μl of distilled water. Kinase reaction is stopped at 4° C., the radioactively labelled probe is then purified over an exclusion column (Bio-Rad Laboratories) which retains the free nucleotides. The transfer membranes are prehybridised for 30 min at 42° C. by incubation in the hybridisation medium (SSC 6×, Denhardt 2×, 25 mM phosphate buffer, 25 mM disodium ethylene diamine tetraacetate or EDTA, SDS 0.1%, 250 μg/ml DNA of salmon sperm) in order to saturate all the non-specific sites. Hybridisation is carried out for 30 min at 42° C. with the internal probe. The membranes are then washed at 42° C. in media of increasing stringency: 10 min in SSC6×/0.1% SDS, 20 min in SSC 2×/SDS 0.1% and 10 min in SSC 0.5×/0.1% SDS. The radioactively labelled membranes sealed in a elastic sheet are then placed in an autoradiography cassette equipped with an amplifying screen. The radioactively labelled bands of cDNA are visualised by reading using a Phosphorimager and are quantified using computer software (Quant Image).

3. Immunodetection of the CRMPs

The anti-peptide antibodies: some specific anti-peptide polyclonal antibodies of the 5 CRMPs were prepared after selection of an immunogen situated in a non-homologous zone for the other CRMPs and injection in a rabbit. The specificity of each serum for a given CRMP was checked by the Western blot method on the recombinant CRMPs. The sera of each of these rabbits, taken before immunisation thereof (pre-immune sera), are negative in the Western blot in the recombinant proteins obtained in Ecolitranes formed or transfected Hela cells and are used as a control. The optimum dilutions for the use thereof were previously determined by the Western blot method or by immunocytochemistry.

Western blot: this technique involves the electrophoretic separation of the proteins then transfer onto a membrane which allows a protein which is of interest to be visualised after the fixing of a specific antibody revealed by a secondary antibody coupled to the peroxidase. Western blots are produced on protein extracts from lysates of immune or nerve cells in culture or freshly isolated. The cells are generally lysed in a buffer without detergent (20 mM Tris-HCl, 10% sucrose, 1 mM EDTA, 5 mM EGTA) and a cocktail of anti-proteases (Complete™ 1×) and sometimes in RIPA buffer (10 mM Tris-HCl pH 7.2, 150 mM of NaCl, 1% of Triton 100×, 0.1% of SDS, 1 mM of EDTA, 1% of sodium deoxycholate, Complete 1×). Homogenisation of the cell lysates was then completed by sonication at 80 Hz. After protein determination, a solution of 1 or 2 μg/μl of proteins is preserved at −20° C. The sample of deposit (final 40 μg of proteins) is denatured by the addition of a reducing buffer (0.0625 M Tris-Hcl pH 6.8, 1% SDS, 10% glycerol, 0.1 M dithiothreitol DTT, bromophenol blue) and heating (5 min at 95° C.). The proteins are separated over SDS acrylamide gel (10%-0.1% respectively). After migration under 100 V, the proteins are electrotransferred onto a nitrocellulose membrane by discontinuous transfer using 3 buffers: buffer 1, 0.3 M Tris base, 20% methanol); buffer 2 (25 mM Tris base, 20% methanol); buffer 3 (25 mM Tris base, 40 mM EACA, 20% methanol) allowing better transfer of all the proteins, whatever their molecular weight. The membranes are incubated for 5 min in a solution of Ponceau red and trichloroacetic acid which allows the proteins to be fixed and visualised. The membranes are then saturated for 1 hour at ambient temperature in a solution of phosphate buffer (PBS)—0.1% Tween 20 and 5% skimmed milk. Immunodetection of the CRMPs with the anti-CRMP polyclonal rabbit sera diluted in PBS, 0.1% Tween 20 and 1% milk (CRMP-4: 1/100; CRMP-2: 1/500; CRMP-1: 1/500; CRMP-3: 1/500; CRMP-5: 1/200) or pre-immune rabbit sera (1/200) is effected at 4° C. for one night. The blots are then rinsed (3×5 min) in PBS, 0.1% Tween 20 and 1% milk then incubated for 1 hour with a specific secondary antibody of the rabbit IgG and coupled with peroxicase (1/50000$^{th}$–1 hour-ambient temperature). After 3 rinses (5 min) in PBS, 0.1% Tween 20 and 1% milk, the blot is revealed in a black chamber using an electrochemiluminescence kit (Covalab) and after printing on photographic film.

During an experiment, the samples were treated with a phosphatase for 1 hour at 37° C. before being separated on an acrylamide/SDS gel: 2 μl of CIP (calf intestinal phosphatase at 20 units/μl) alkaline phosphatase are added to 20 μl of protein sample and to 2 μl of buffer, allowing enzyme activity.

Immunocytochemistry (ICC): the CRMPs were detected on a cellular scale by immunocytochemistry. The lymphocytes, which are non-adhesive cells, are spread by centrifugation (cytospin-600 rpm-5 min) whereas the Dev nerve cells are cultivated on Permanox slides (Labteck). Fixing of the cells by acetone (−20° C., 5 min) has the object of fixing the proteins and making the cells permeable to the entry of the reactive antibodies. These conditions enabled the CRMP 1, 2, 3, 4 and 5 to be detected. The non-specific sites are blocked with a 0.1% solution of BSA (30 minutes at ambient temperature). First contact of the cells fixed on slides is made with the primary antibody (anti-CRMP produced in rabbits, diluted in PBS, pH 7.4) (1 h-37° C. in a moist chamber). After washing three times in phosphate buffer (PBS, pH 7.4, 5 min), the specific secondary antibody of the rabbit IgG is placed in contact (1 h-ambient temperature) and washed three times in PBS for 5 min. The counterstaining of the nuclei is then effected by incubation in a Dapi solution (nucleic intercalator-0.025 μg/ml-1 min). The slides are mounted in glycerol buffered to pH 7.4. The results of these analyses are shown in FIG. 2 to 8.

EXAMPLE 1

Evaluation of the Expression of CRMP 1, 2 and 4 in Mononucleated Lymphocytes and Cells, Control Lymphocytes and Cells or Lymphocytes and Cells Derived from Patients Affected by Dysimmune Pathologies mRNA (relative to GAPDH)

A first evaluation was made by titrating the corresponding mRNA. The results are presented in detail in FIG. 1 and summarised in Table I below.

Comparative Profile, Considering all the Samples for the Same CRMP:

TABLE I

|  | CRMP2 | CRMP4 | CRMP1 |
| --- | --- | --- | --- |
| Control T lines | + | 0 | 0 |
| T/HTLV-1 lymphocytes | ++ | +++ | +++ |
| "Control" patients lympho. | ± | 0 | ± |
| Apopt. defic. patients lympho. | ± | 0 | +/++ |
| HIV patients | ++ | ++ | ++ |

The foregoing analysis is completed by detecting CRMP 1, 2 and 4 proteins in T lymphocytes and nerve cells by a Western blot on a cell lysate (Dev: nerve cells; Jurkat; T lymphocyte line) in non-detergent buffer and using the specific antipeptide polyclonal antibodies of each CRMP.

The results are presented in FIG. 2.

It will be noted that the anti-CRMP-1, -2 and -4 detect a plurality of isoforms shared by the T lymphocytes and the nerve cells.

EXAMPLE 2

Immunocytochemical detection of the subcellular location of the CRMP2 protein in mononucleated blood cells (PBL) of control patients or patients infected with HTLV-1 or having an immune deficiency associated with the Fas/Fas ligand system or infected with HIV.

The anti CRMP-2 antibody was previously prepared and isolated by the protocol described in item 3 of the preamble of "equipment and method".

The results are illustrated in FIG. 3.

It will be noted that:

the location of CRMP-2 is essentially cytoplasmic in the lymphocytes (PBL) isolated from a control subject or from a subject infected with HIV-1; it may also be nuclear in the lymphocytes isolated from patients infected with HTLV-1 or in the PBL of a dysimmune patient (Fas deficiency);

CRMP-2 is expressed more in the lymphocytes of patients than in those of the control subject cultivated in the IL2 and therefore preactivated.

By examination after immunodetection of CRMP-2 and counter-staining by the intercalator of Dapi DNA, it is noted that the expression is largely nuclear in the hyperproliferative T lymphocytes which are chronically infected with RTLV-1. Examination of CRMP-2 immunodetection by confocal microscopy reveals a very weak nuclear presence in the control T lymphocytes and a majority nuclear presence in the T lymphocytes chronically infected with HTLV-1 (FIG. 4).

To conclude, the expression of CRMP2 is increased in the nuclei of proliferative lymphocytes. On the other hand, CRMP2 remains cycloplasmic in patients infected with HIV. The location is nuclear in some cells in dysimmune patients (Fas deficient). FIGS. 3 and 4 show the results obtained.

Similarly, the nuclear presence of a protein recognised by this same antibody has been checked in the hyperproliferative T lymphocytes by a Western blot on cell fractions enriched in nuclei.

EXAMPLE 3

Characterisation by Immunohystochemistry of the Expression of the CRMP5 and CRMP2 Proteins Over the Thymus The proteins were characterised by means of their respective antibodies.

The analysed cells are cells of normal human fetus thymus and in a thymoma in an adult patient.

As a control, the same immunohystochemistry was carried out on human thymus of a six-week old embryo. The thymus is deep-frozen and sectioned in a cryostat (15 µm). The sections are fixed for 15 minutes in acetone. Immunohystochemistry is carried out under the same conditions as on the brain.

This analysis reveals an expression of CRMP2 and CRMP5 in the thymic epithelial cells which is normal at the embryonic stage. The expression disappears in normal adults and may be induced in the case of tumoral pathology (thymoma).

EXAMPLE 4

Characterization of the Interaction Between Bovine PrP Protein and Human CRMP5 Protein The interaction between bovine PrP protein and human CRMP5 protein was characterised by two-hybrid tests by conjugation.

The cDNA which are encoding these two proteins (complete or different derived forms) were cloned in a "bait" vector and a "prey" vector. The bait vector pEG202 (Gyuris et al, 1993, Cell 75, 791-803) comprises the gene encoding the marker HIS3, an origin of replication 2µ and directs the expression of proteins merged with the range of association with the DNA of the LexA protein (1-202), under the control of the constituent promoter ADHp. The prey vector, pJG 4-5 (U.S. Pat. No. 5,580,736), comprises the gene encoding the marker TRP1, an origin of replication 2 microns and directs the expression of merged proteins to a nuclear location sequence (NLS) to the transcription activating range (B42) and to the epitope HA under the control of the inducible promoter GALP. For convenience, the fusion NLS-B42-HA is designated "Act" here.

The strain EGY42 (MATα) (Golemis et al, 1992, Mol. Cell. Biol. 12, 3006-3014) was co-transformed with the plasma vector pSH-18-34 (U.S. Pat. No. 5,695,941) comprising the marker gene URA3 and eight LexA operators placed upstream of the reporter gene lacZγ and various bait vectors directing the expression of LexA, LexA-PrP, LexA-PrPm (mutations on PrP still to be determined), LexA-PrPtr (truncation of PrP still to be determined), LexA-MAX (negative control) and LexA-CRMP5.

The strain EGY48 (MATα) was transformed with various prey vectors directing the expression of Act, Act-PrP, Act-BaxΔTM (negative control) and Act-CRMP5.

These various strains were conjugated so as to create an interaction matrix.

This matrix was replicated on an indicator medium (Ura⁻, His⁻, Trp⁻, galactose/X-gal) allowing expression of the baits and the preys, selection of the diploid exconjugants and revelation of the interaction phenotypes (colour blue, revealing β-galactosidase activity observed when the reporter gene lacZ is transcribed).

FIG. 7 shows the results obtained.

The following constructions were tested:

PrP: bovine PrP protein (AA 22-237),

PrP: bovine PrP protein (AA 22-237) containing various mutations which are still to be determined, PrPtr: bovine PrP protein (AA-22-?), truncated toward the middle of the sequence (the position of the codon is still to be determined), MAX: negative interaction control CRMP 5: complete human CRMP 5 protein BAXΔTM: negative interaction control.

The interaction between the PrP proteins (various constructions detailed below) and the CRMP5 protein is detected when the PrP proteins are expressed as baits and the CRMP5 protein is expressed as prey. LexA-CRMP5 and Act-Prp do not give an interaction phenotype. The negative controls (LexA-MAX and Act-BaxΔTM as well as LexA and Act) do not give an interaction phenotype with the PrP and CRMPs. The homodimerisation of CRMP5 provides the positive interaction control of this matrix.

EXAMPLE 5

Effect of the CRMP on the Migration of the T Lymphocytes

Method

The migration of the T lymphocytes (Jurkat) is evaluated after transfection or non-transfection of plasmid encoding various forms of CRMP-2: gfb associated CRMP2: cmyc associated CRMP-2 and mutated CRMP-2, Delta381CRMP-2 (deletion of amino acids 381 to 572 containing on a TyrKin site, a SH3 binding site and the site of adhesion to the tubulin heterodimers (Fukata et al. Nat Cell Biol, 2002, Aug. 4(8):583-91). The transfection is verified by the detection of GFP and of cmyc in the cells before and after migration by a Western blot.

Migration takes place in a Boyden chamber (3 micron pores) for 18 hours in the standard RPMI medium+foetal calf serum. 400,000 cells are deposited in the upper well and the number of cells which have migrated into the lower well is counted (triple wells, three experiments with CRMP-2gfp and two with cmyc CRMP2). The base level of migration is that obtained with the cells transfected with a plasmid not containing the CRMP-2 insert.

The CRMP/vimentin association is visualised by immunoprecipitation and a Western blot (IP vimentin Wester CRMP) and co-immunodetection on migrating or non-migrating T lymphocyte cells (confocal microscopy).

Results

The over-expression of gfp CRMP-2 or cmyc CRMP-2 in the Jurkats increases the number of cells which have migrated in 6 hours and 18 hours (FIGS. 9 and 10).

The mutation of Delta381 CRMP-2 (site containing Tyr-Kin and the tubuline binding site) amplifies the migration, suggesting a role of this range in migration (FIG. 11).

The CRMP-2 is the partner of vimentin (cytoskeleton protein), suggesting the participation of CRMP-2 in the reclassification of the cytoskeleton.

The invention claimed is:

1. A method for in vitro screening for a pathology involving a dysfunction of the T lymphocytes, said method comprising:
   a) evaluating the level of expression, the location, or the phosphorylation of a Collapsin Response Mediator Protein (CRMP) in cells of the immune system taken from a patient; and
   b) comparing the level of expression, location or the phosphorylation of said CRMP with the level of expression, location or the phosphorylation of said Collapsin Response Mediator Proteins in control cells of the immune system from a healthy subject, wherein an increased expression, or modified location, or modified phosphorylation of said CRMP in the cells of the immune system taken from said patient as compared to the expression, the location or the phosphorylation of said CRMP in the control cells of the immune system obtained from said healthy subject is indicative of a pathology involving a dysfunction of the T lymphocytes, wherein the Collapsin Response Mediator Protein is CRMP2 or CRMP5, and wherein said pathology is selected from the group consisting of:
   T leukaemias and lymphomas,
   viral infections, wherein the viral infection is selected from the group consisting of measles virus and HTLV-1; and
   multiple sclerosis.

2. The method according to claim 1, wherein said cells of the immune system are selected from lymphocytes, dendritic cells and monocytes.

3. The method according to claim 1, further comprising the steps of:
   contacting a biological sample containing mRNA, obtained from lymphocytes in a patient, with oligonucleotides allowing the amplification of all or part of the transcript of the gene encoding a CRMP;
   amplifying said transcript; and
   detecting and quantifying the amplification products,
wherein an increase of the transcript rate of the CRMP relative to a normal control is indicative of said pathology involving a dysfunction of the T lymphocytes, or of a predisposition to develop such a pathology.

4. The method according to claim 1, wherein the level of expression, the location or the phosphorylation of the CRMP in lymphocytes is evaluated by contacting of at least one antibody directed against the CRMP with a sample of lymphocytes under conditions which allow the possible formation of specific immunological complexes between the CRMP and said antibody or antibodies and the detection of the specific immunological complexes possibly formed and/or the inhibition of CRMP activity by the antibody, wherein an increased expression or modified location or modified phosphorylation of said CRMP in the lymphocytes taken from said patient as compared to the expression, the location or the phosphorylation of said CRMP in the lymphocytes obtained from said healthy subject is indicative of said pathology involving a dysfunction of the T lymphocytes.

5. The method according to claim 1, wherein the increased expression or modified location or modified phosphorylation of the CRMP is detected with an antibody directed against the CRMP.

6. The method according to claim 5, wherein the antibody directed against the CRMP is an antibody directed against a peptide of sequence SEQ ID NO:24, SEQ ID NO:28 or SEQ ID NO:27.

7. The method according to claim 1, wherein an increased expression of said CRMP in the cells of the immune system taken from said patient as compared to the expression of said CRMP in the control cells of the immune system obtained from said healthy subject is indicative of said pathology involving a dysfunction of the T lymphocytes.

8. The method according to claim 1, wherein an increased nuclear translocation of said CRMP in the cells of the immune system taken from said patient as compared to the location of said CRMP in the control cells of the immune system obtained from said healthy subject is indicative of said pathology involving a dysfunction of the T lymphocytes.

9. The method according to claim 1, wherein an increased phosphorylation of said CRMP in the cells of the immune system taken from said patient as compared to the phosphorylation of said CRMP in the control cells of the immune system obtained from said healthy subject is indicative of said pathology involving a dysfunction of the T lymphocytes.

* * * * *